United States Patent
Chepuri et al.

(10) Patent No.: US 9,981,923 B2
(45) Date of Patent: May 29, 2018

(54) 1,2,3 TRIAZOLE ANTIFUNGAL AGENTS AND PREPARATION THEREOF

(71) Applicant: COUNCIL OF SCIENTIFIC & INDUSTRIAL RESEARCH, New Delhi (IN)

(72) Inventors: Venkata Ramana Chepuri, Maharashtra (IN); Mukund Vinayak Deshpande, Maharashtra (IN); Santosh Genba Tupe, Maharashtra (IN); Yadagiri Kommagala, Maharashtra (IN)

(73) Assignee: Council of Scientific & Industrial Research, New Dehi (IN)

( * ) Notice: Subject to any disclaimer, the term of this patent is extended or adjusted under 35 U.S.C. 154(b) by 0 days. days.

(21) Appl. No.: 15/320,590

(22) PCT Filed: Jun. 18, 2015

(86) PCT No.: PCT/IN2015/000249
§ 371 (c)(1),
(2) Date: Dec. 20, 2016

(87) PCT Pub. No.: WO2015/193915
PCT Pub. Date: Dec. 23, 2015

(65) Prior Publication Data
US 2017/0197924 A1    Jul. 13, 2017

(30) Foreign Application Priority Data

Jun. 20, 2014 (IN) .......................... 1660/DEL/2014

(51) Int. Cl.
*C07D 249/06* (2006.01)
*A01N 43/647* (2006.01)

(52) U.S. Cl.
CPC ......... *C07D 249/06* (2013.01); *A01N 43/647* (2013.01)

(58) Field of Classification Search
None
See application file for complete search history.

(56) References Cited

U.S. PATENT DOCUMENTS 3,579,531 A    5/1971 Scheiner
4,098,894 A    7/1978 Büchel et al.
2012/0101096 A1    4/2012 Hedstrom et al.

FOREIGN PATENT DOCUMENTS

CN    102796052 A    11/2012

OTHER PUBLICATIONS

International Search Report (ISR) for PCT/IN2015/000249; I.A. fd: Jun. 18, 2015, dated Oct. 14, 2015, European Patent Office, Rijswijk, Netherlands.
International Preliminary Report on Patentability (IPRP) including the Written Opinion of the International Searching Authority (PCT Rule 44bis) for PCT/IN2015/000249; I.A. fd: Jun. 18, 2015, dated Dec. 20, 2016, by the International Bureau of WIPO, Geneva, Switzerland.
Lima-Neto, RG et al., "Synthesis of 1,2,3-Triazole Derivatives and in Vitro Antifungal Evaluation on Candida Strains," Molecules 2012, 17(5), 5882-5892; doi:10.3390/molecules17055882, May 16, 2012, MDPI, Basel, Switzerland.
Guar, M et al., "Synthesis, characterization, and antifungal activity of biaryl-based bis(1,2,3-triazoles) using click chemistry," Monatshefte für Chemie—Chemical Monthly, Feb. 2012, vol. 143, Issue 2, pp. 283-288, Springer-Verlag, Wein, NY.

*Primary Examiner* — Alicia L Otton
(74) *Attorney, Agent, or Firm* — Sterne, Kessler, Goldstein & Fox P.L.L.C.

(57) ABSTRACT

The present application relates to 1,4-disubstituted 1,2,3-Triazole antifungal agents of the formula (I) wherein, R1 is halogens such as fluorine, chlorine or bromine, CF3, alkyl; R2 is alkyl or hydrogen; R3 is halogen selected from fluorine, chlorine or bromine; and n is 0 or 1. The application further relates to the synthesis of said compounds, to fungicidal compositions containing said compounds and to their use in a method for treating fungal infections.

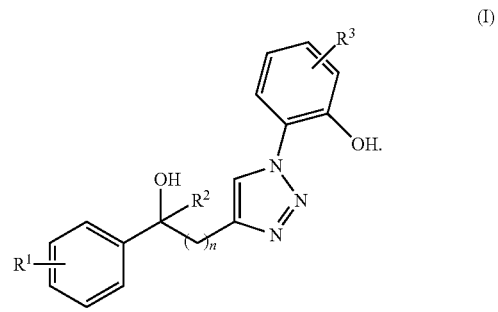

7 Claims, 2 Drawing Sheets

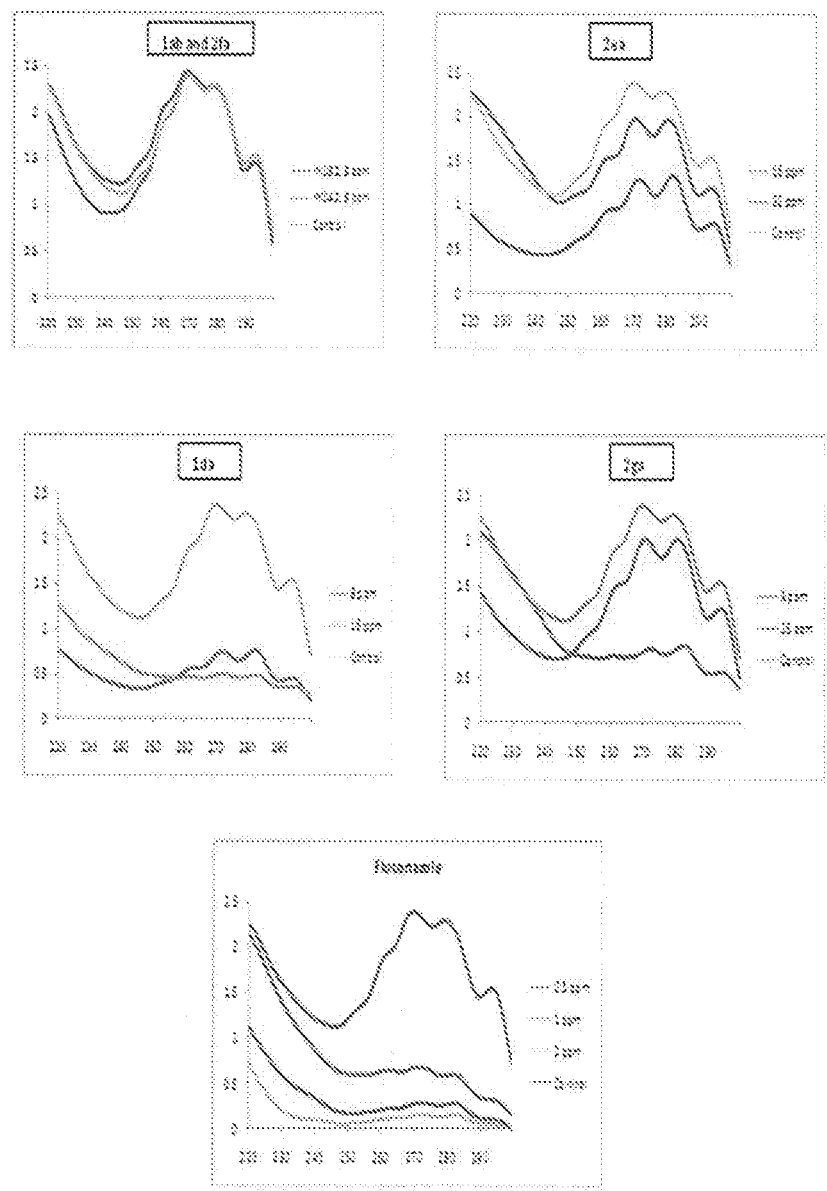
Fig: 1

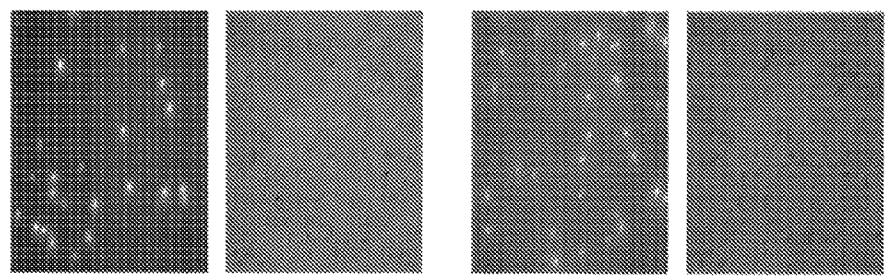
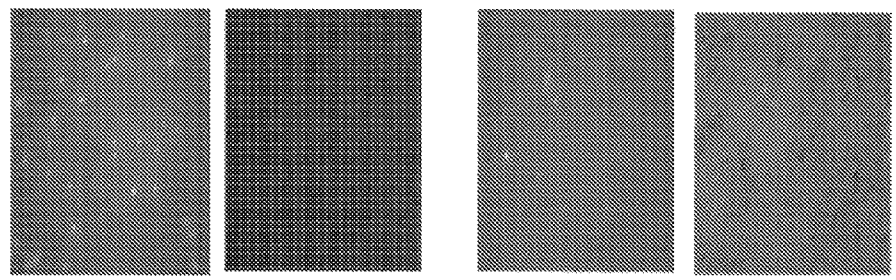
Fig: 2

1,2,3 TRIAZOLE ANTIFUNGAL AGENTS AND PREPARATION THEREOF

FIELD OF THE INVENTION

The present invention relates to novel triazole antifungal agents of the formula (I).

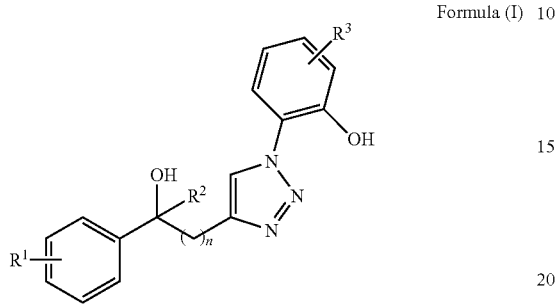

Formula (I)

Wherein, $R_1$ is halogens such as fluorine, chlorine or bromine, $CF_3$, alkyl;
$R_2$ is alkyl or hydrogen;
$R_3$ is halogen selected from fluorine, chlorine or bromine; and n is 0 or 1.

The present invention also relates to a process for the preparation of the novel antifungal agents of the formula (I) from alkynols and 2-azidophenols.

BACKGROUND AND PRIOR ART

Triazole moiety is an important and frequent insecticide, agrochemical structure feature of many biological active compound as cytocrome p450 enzyme inhibitors and peptide analog inhibitor. The azole class of antifungal agent is chemical either an imidazole or a triazole group joined to an asymmetric carbon atom as their functional pharmacophore treatment for these infection azole like antifungal agent are Ketoconazole, Fluconazole, Voriconazole and Itraconazole 1, 2, 4-triazole are as analgesic antiasthmatic, antibacterial, anticholinergic activity. They are aromatic ring compounds similar to the azole, pyrazole and imidazole but with an additional nitrogen atom in the ring structure. Like the azoles, triazoles are used in many antifungal drugs and fungicides, but the triazole-based drugs are more selective for fungi than mammalian cells than the azole-based antifungal compounds.

In recent years, triazole-containing compounds have become potential targets for drug discovery. 1,2,3-triazole moiety is an important pharmacophore present in diverse medicinally important molecules with potential applications as anticancer, HIV protease inhibitors, anti-tubercular, antibacterials, and as a core structure of azole class of antifungal drugs (Agalave et al., 2011). There were very few antifungal agents (mainly polyenes) in clinical use till 1980. The development of azoles namely; ketoconazole, miconazole, fluconazole in 80's and itraconazole, posaconazole, voriconazole in 90's resulted in rapid advancement of antifungal therapy. These azoles were effective against fungal pathogens that were refractory to the polyenes and available both in intravenous and oral formulations. However over the years, many fungal pathogens developed resistance against fluconazole and other azoles due to their wide use as first line drugs in treatment. Triazole analogues of several bioactive compounds have recently been reported. Examples are those of the well-known highly functionalized antiviral cyclic amino acid derivatives oseltamivir and zanamivir. The 1,2,3-triazole moiety is a constituent part of many modified nucleosides or carbanucleosides with antiviral, anti-HIV or cytostatic activities. However, the scope of triazole chemistry is not confined to drug discovery.

Article titled "Regio-selective synthesis of 1,4-disubstituted-1,2,3-triazoles and evaluation of their antimicrobial activity" by R Parveen et al. published in *Asian Journal of Biomedical and Pharmaceutical Sciences*, 15 Jun. 2014, 4(32), 44-47 reports a series of 1,4-disubstituted 1,2,3-triazoles synthesized via Cu(I) catalyzed reaction between terminal alkyne and substituted phenyl azides. The synthesized triazoles are characterized by 1 H NMR and mass spectral techniques. The synthesized compounds are evaluated for their antimicrobial activity against *Escherichia coli, Staphylococcus aureus, Aspergillus niger* by well diffusion method.

Article titled "Regioselective syntheses of fully-substituted 1,2,3-triazoles: the CuAAC/C-H bond functionalization nexus" by L Ackermann et al. published in *Org. Biomol. Chem.*, 2010,8, 4503-4513 reports regioselective synthesis of 1,4,5-trisubstituted 1,2,3-triazoles by three different strategies, relying on (i) the interception of stoichiometrically formed 5-cuprated- 1,2,3-triazoles, (ii) the use of stoichiometrically functionalized alkynes or (iii) catalytic C—H bond functionalizations.

Article titled "Efficient continuous-flow synthesis of novel 1,2,3-triazole-substituted β-aminocyclohexanecarboxylic acid derivatives with gram-scale production" by S B Otvös et al. published in *Beilstein J Org Chem*, 2013, 9, pp 1508-16 reports preparation of novel multi-substituted 1,2,3-triazole-modified β-aminocyclohexanecarboxylic acid derivatives in a simple and efficient continuous-flow procedure. The 1,3-dipolar cycloaddition reactions are performed with copper powder as a readily accessible Cu(I) source. Initially, high reaction rates was achieved under high-pressure/high-temperature conditions. Subsequently, the reaction temperature was lowered to room temperature by the joint use of both basic and acidic additives to improve the safety of the synthesis, as azides were to be handled as unstable reactants.

Most useful and powerful procedure for the synthesis of 1,2,3-triazoles is the Huisgen 1,3-dipolar cycloaddition of organic azides with acetylenes. The classical Huisgen reaction, thermally induced, gives an approximate 1:1 mixture of 1,4- and 1,5-disubstituted 1,2,3-triazole isomers. However, when Cu(I) catalysis is applied, the reaction becomes regioselective, exclusively yielding the 1,4-regioisomer within a relatively short reaction time. Recently, Cu(I)-catalyzed azide-alkyne cycloaddition (CuAAC) has become the basis of the so-called click chemistry concept due to its wide applicability and efficiency.

Moreover, other drawbacks associated with azoles, such as narrow spectrum, low oral bioavailability, drug-drug interactions, and hepatic toxicity reduced their efficacy and needs to be overcome.

Therefore, there is need for development of new azole derivatives with broad spectrum activity and better efficacy and safety. Accordingly the inventors have designed three classes of 1,2,3 -triazole compounds as novel anti-fungal agents. These compounds are easy to synthesize from simple starting materials, processes are green, convergent, carried at room temperature and highly scalable.

OBJECTIVE OF INVENTION

The main objective of the present invention is to provide a novel triazole antifungal agents of formula (I).

Another objective of the present invention is to provide a process for the synthesis of novel triazole antifungal agents of formula (I).

SUMMARY OF THE INVENTION

Accordingly, the present invention provides a novel triazole antifungal agents of formula (I).

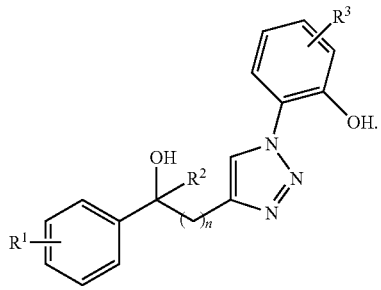

Formula (I)

Wherein, $R_1$ is halogens such as fluorine, chlorine or bromine, $CF_3$, alkyl;
$R_2$ is alkyl or hydrogen;
$R_3$ is halogen selected from fluorine, chlorine or bromine; and n is 0 or 1.

In an aspect, the present invention provides a process for the synthesis of novel triazole antifungal agents of formula (I) from alkynols and 2-azidophenols.

BRIEF DESCRIPTION OF THE DRAWINGS

FIG. 1 depicts Absorbance spectrum.
FIG. 2 depict ROS production in *C. albicans* ATCC 24433.

DETAILED DESCRIPTION OF THE INVENTION

The invention will now be described in detail in connection with certain preferred and optional embodiments, so that various aspects thereof may be more fully understood and appreciated.

The present invention provides a novel triazole antifungal agents of formula (I) and process for preparation thereof.

In an embodiment, the present invention provides a novel antifungal agents compound of formula (I) (1/Type-I or 2/Type-II),

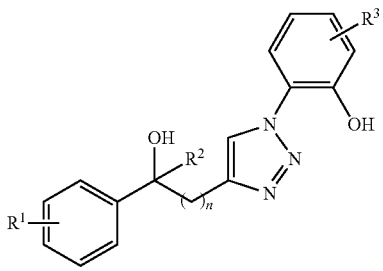

Formula (I)

Wherein, $R_1$ is halogens such as fluorine, chlorine, bromine, $CF_3$, alkyl;
$R_2$ is alkyl or hydrogen;
$R_3$ is halogen selected from fluorine, chlorine or bromine; and n is 0 or 1.

In another preferred embodiment, the compounds of formula (I) are:
i. 4-Chloro-2-(4-((3,5-dimethylphenyl)(hydroxy)methyl)-1H-1,2,3-triazol-1-yl)phenol (1aa).
ii. 2-(4-((3,5-Bis(trifluoromethyl)phenyl)(hydroxy)methyl)-1H-1,2,3-triazol-1-yl)-4-chlorophenol(1ba),
iii. 4-Chloro-2-(4-(1-hydroxy-1-phenylpropyl)-1H-1,2,3-triazol-1-yl)phenol,
iv. 5-Chloro-2-(4-((3,5-dimethylphenyl)(hydroxy)methyl)-1H-1,2,3-triazol-1-yl)phenol(1ab),
v. 5-Chloro-2-(4-(1-hydroxy-1-phenylethyl)-1H-1,2,3-triazol-1-yl)phenol(2cb),
vi. 4-Chloro-2-(4-(2-hydroxy-2-phenylethyl)-1H-1,2,3-triazol-1-yl)phenol(1ea),
vii. 5-Chloro-2-(4-(2-hydroxy-2-phenylethyl)-1H-1,2,3-triazol-1-yl)phenol(1eb),
viii. 4-Chloro-2-(4-(2-hydroxy-2-phenylpropyl)-1H-1,2,3-triazol-1-yl)phenol(2fa),
ix. 5-Chloro-2-(4-(2-hydroxy-2-phenylpropyl)-1H-1,2,3-triazol-1-yl)phenol(2fb),
x. 4-Chloro-2-(4-(2-hydroxy-2-phenylbutyl)-1H-1,2,3-triazol-1-yl)phenol(2ga),
xi. 5-Chloro-2-(4-(2-hydroxy-2-phenylbutyl)-1H-1,2,3-triazol-1-yl)phenol(2gb),
xii. 4-chloro-2-(4-(2-hydroxy-2-phenylhexyl)-1H-1,2,3-triazol-1-yl)phenol(2ha),
xiii. 4-Chloro-2-(4-(2-hydroxy-2,2-diphenylethyl)-1H-1,2,3-triazol-1-yl)phenol(2ia),
xiv. 5-Chloro-2-(4-(2-hydroxy-2,2-diphenylethyl)-1H-1,2,3-triazol-1-yl)phenol(2ib),
xv. 2-(4-(2-(3,5-Bis(trifluoromethyl)phenyl)-2-hydroxyethyl)-1H-1,2,3-triazol-1-yl)-4-chlorophenol(1ja),
xvi. 2-(4-(2-(3,5-Bis(trifluoromethyl)phenyl)-2-hydroxyethyl)-1H-1,2,3-triazol-1-yl)-5-chlorophenol(1jb),
xvii. 2-(4-(2-(3,5-Bis(trifluoromethyl)phenyl)-2-hydroxypropyl)-1H-1,2,3-triazol-1-yl)-4-chlorophenol(2sa),
xviii. 2-(4-(2-(3,5-Bis(trifluoromethyl)phenyl)-2-hydroxypropyl)-1H-1,2,3-triazol-1-yl)-5-chlorophenol(2sb),
xix. 4-Chloro-2-(4-(2-(2,4-difluorophenyl)-2-hydroxypropyl)-1H-1,2,3-triazol-1-yl)phenol(2ka),
xx. 4-Chloro-2-(4-(2-(2,4-dichlorophenyl)-2-hydroxypropyl)-1H-1,2,3-triazol-1-yl)phenol(2ma),
xxi. 4-Chloro-2-(4-(2-(4-(dimethylamino)phenyl)-2-hydroxyethyl)-1H-1,2,3-triazol-1-yl)phenol (2pa),
xxii. 5-Chloro-2-(4-(2-(2,4-difluorophenyl)-2-hydroxypropyl)-1H-1,2,3-triazol-1-yl)phenol (2kb),
xxiii. 5-Chloro-2-(4-(2-(2,4-dichlorophenyl)-2-hydroxypropyl)-1H-1,2,3-triazol-1-yl)phenol (2mb),
xxiv. 5-Chloro-2-(4-(2-(2-fluoro-4-(trifluoromethyl)phenyl)-2-hydroxyethyl)-1H-1,2,3-triazol-1-yl)phenol (2ob),
xxv. 2-(4-(2-(2,4-Difluorophenyl)-2-hydroxypropyl)-1H-1,2,3-triazol-1-yl)-5-fluorophenol (2kc),
xxvi. 2-(4-(2-(2,4-Dichlorophenyl)-2-hydroxypropyl)-1H-1,2,3-triazol-1-yl)-5-fluorophenol (2mc),
xxvii. 5-Fluoro-2-(4-(2-(2-fluoro-4-(trifluoromethyl)phenyl)-2-hydroxyethyl)-1H-1,2,3-triazol-1-yl)phenol (2oc),
xxviii. 5-Fluoro-2-(4-(2-(4-fluorophenyl)-2-hydroxypropyl)-1H-1,2,3-triazol-1-yl)phenol (2qc),
xxix. 2-(4-(2-(4-Chlorophenyl)-2-hydroxypropyl)-1H-1,2,3-triazol-1-yl)-5-fluorophenol (2lc),
xxx. 2-(4-(2-(4-Bromophenyl)-2-hydroxypropyl)-1H-1,2,3-triazol-1-yl)-5-fluorophenol (2nc),
xxxi. 4-Chloro-2-(4-(2-(4-fluorophenyl)-2-hydroxypropyl)-1H-1,2,3-triazol-1-yl)phenol (2qa),
xxxii. 4-Chloro-2-(4-(2-(4-chlorophenyl)-2-hydroxypropyl)-1H-1,2,3-triazol-1-yl)phenol (2la), xxxiii. 2-(4-(2-(4-Bromophenyl)-2-hydroxypropyl)-1H-1,2,3-triazol-1-yl)-4-chlorophenol (2na),
xxxiv. 5-Chloro-2-(4-(2-(4-fluorophenyl)-2-hydroxypropyl)-1H-1,2,3-triazol-1-yl)phenol (2qb),
xxxv. 5-Chloro-2-(4-(2-(4-chlorophenyl)-2-hydroxypropyl)-1H-1,2,3-triazol-1-yl)phenol (2lb),
xxxvi. 2-(4-(2-(4-Bromophenyl)-2-hydroxypropyl)-1H-1,2,3-triazol-1-yl)-5-chlorophenol (2nb),
xxxvii. 2-(4-(2-(4-Fluorophenyl)-2-hydroxypropyl)-1H-1,2,3-triazol-1-yl)phenol (2qd),
xxxviii. 2-(4-(2-(4-Chlorophenyl)-2-hydroxypropyl)-1H-1,2,3-triazol-1-yl)phenol (2ld),
xxxix. 2-(4-(2-(4-Bromophenyl)-2-hydroxypropyl)-1H-1,2,3-triazol-1-yl)phenol (2nd)
xl. 2-(4-(2-(2,4-Difluorophenyl)-2-hydroxypropyl)-1H-1,2,3-triazol-1-yl)phenol (2kd)
xli. 2-(4-(2-(2,4-Dichlorophenyl)-2-hydroxypropyl)-1H-1,2,3-triazol-1-yl)phenol (2md).

In one embodiment, the present invention provides a process for the synthesis of novel triazole compounds of formula (I), with >75% yields comprising the steps of:
a. Adding sodium ascorbate and copper (II) sulfate to a solution of 2-azidophenols 5 and alkyne 4 or 7 in $^tBuOH:H_2O$ and stirring the resulting brick reddish mixture vigorously to obtain the reaction mixture;
b. Work-up and purification of the completed reaction mixture of step (a) to afford the desired product.

The above process is shown below in Scheme 1:

Scheme 1: Type I and Type-II 1,2,3-triazoles

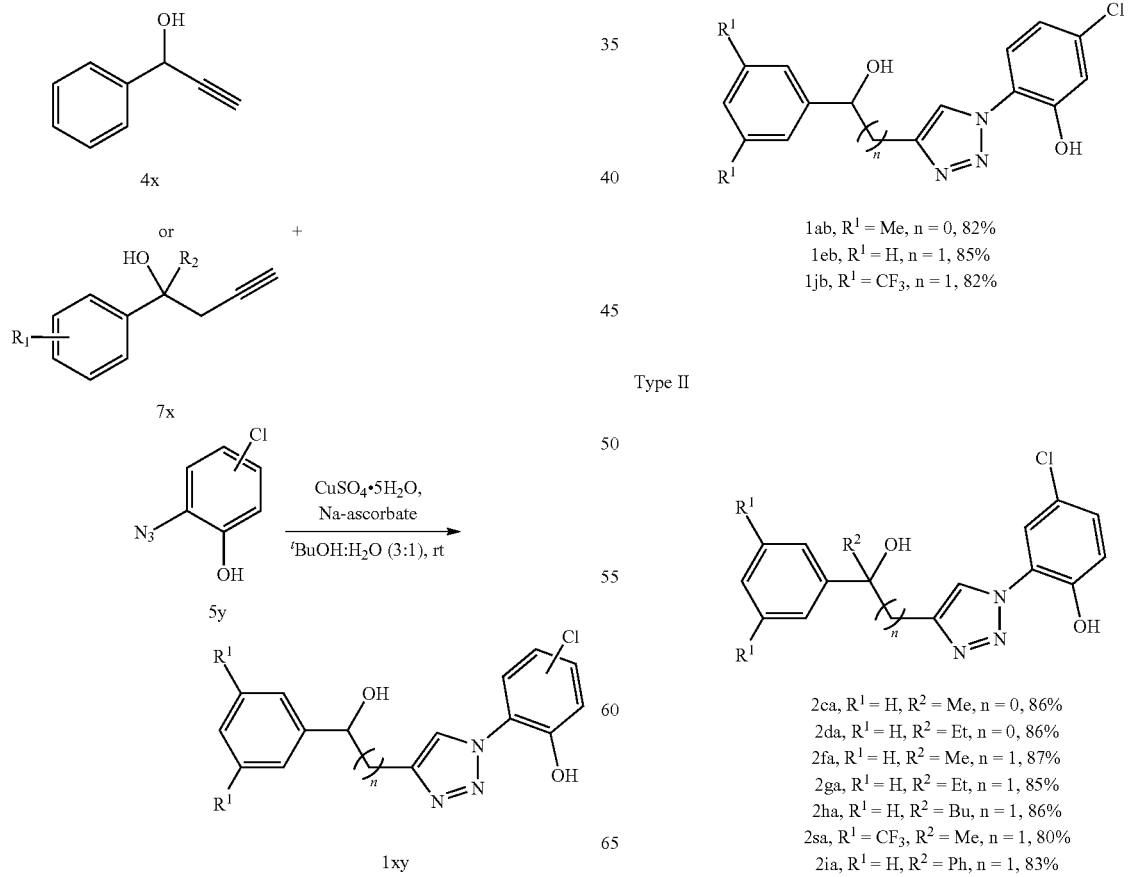

Type-I

1aa, $R^1$ = Me, n = 0, 86%
1ba, $R^1$ = CF$_3$, n = 0, 84%
1ea, $R^1$ = H, n = 1, 83%
1ja, $R^1$ = CF$_3$, n = 1, 87%

1ab, $R^1$ = Me, n = 0, 82%
1eb, $R^1$ = H, n = 1, 85%
1jb, $R^1$ = CF$_3$, n = 1, 82%

Type II

2ca, $R^1$ = H, $R^2$ = Me, n = 0, 86%
2da, $R^1$ = H, $R^2$ = Et, n = 0, 86%
2fa, $R^1$ = H, $R^2$ = Me, n = 1, 87%
2ga, $R^1$ = H, $R^2$ = Et, n = 1, 85%
2ha, $R^1$ = H, $R^2$ = Bu, n = 1, 86%
2sa, $R^1$ = CF$_3$, $R^2$ = Me, n = 1, 80%
2ia, $R^1$ = H, $R^2$ = Ph, n = 1, 83%

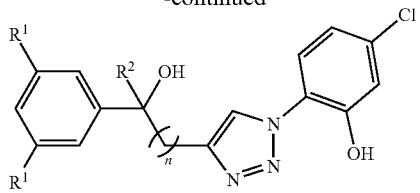
2cb, R¹ = H, R² = Me, n = 0, 79%
2fb, R¹ = H, R² = Me, n = 1, 83%
2gb, R¹ = H, R² = Et, n = 1, 80%
2sb, R¹ = CF₃, R² = Me, n = 1, 84%
2ib, R¹ = H, R² = Ph, n = 1, 81%
The 2-azidophenols is selected from the group of compounds consisting of formula 5y.
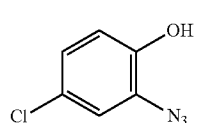
5a
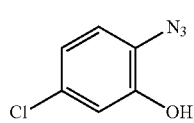
5b
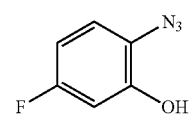
5c
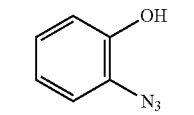
5d
The alkyne is selected from the group of compounds consisting of formula 4x or 7x.
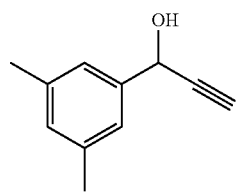
4a
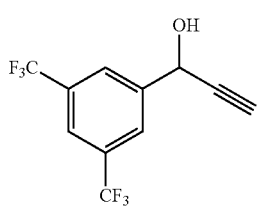
4b
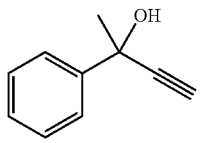
4c
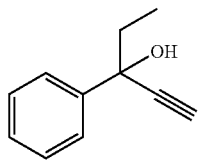
4d
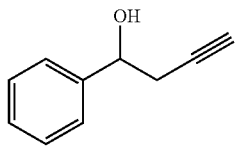
7e
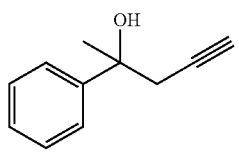
7f
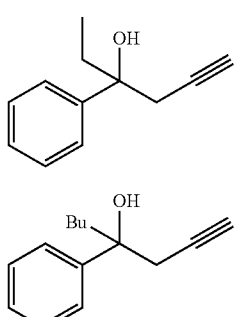
7g
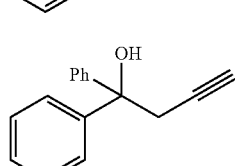
7h
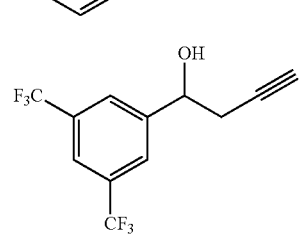
7i
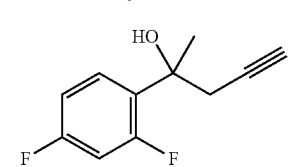
7j
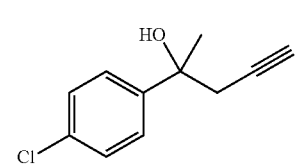
7k
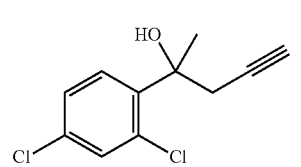
7l
7m -continued

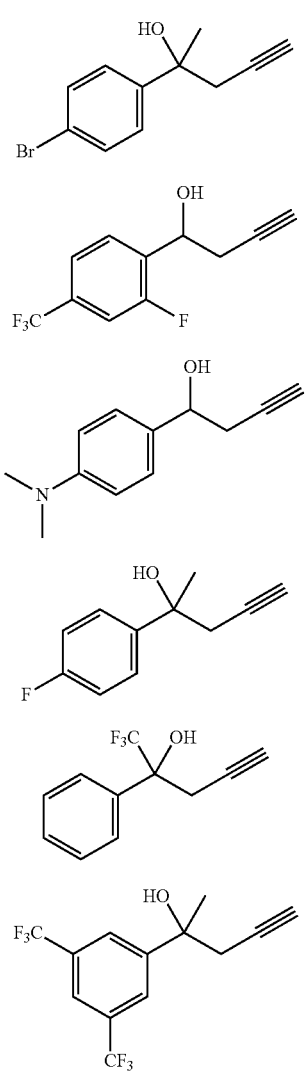

7n

7o

7p

7q

7r

7s

In another embodiment, the invention discloses use of compounds of Formula (I) as antifungal agents.

In another preferred embodiment, the invention discloses pharmaceutical preparations which comprise a compound of Formula (I) in association with at least one pharmaceutical excipient known in art. These excipients are added to the composition for a variety of purposes.

The pharmaceutical preparations can be selected from various dosage forms such as solid dosage form like tablets, capsules, pellets, powders, soft gelatin capsules, and the like and oral liquids. The tablets can be prepared as conventional dosage forms such as immediate release, sustained release, modified release or controlled release.

The pharmaceutical compositions can be prepared using conventional techniques well known in the art.

According to another embodiment, the invention provides method for treating or preventing antifungal infections in a subject, wherein said method comprises administering therapeutically effective amounts of the compounds of formula (I) of the present invention or pharmaceutical composition comprising the same. The compounds of the present invention can also be administered optionally with other actives depending on the disease conditions.

As used herein the term "therapeutically effective amount" means an amount used in the pharmaceutical preparations to achieve the desired therapeutic effect.

The amount/quantity of the compound used in pharmaceutical compositions of the present invention will vary depending upon the body weight of the patient and the mode of administration and can be of any effective amount to achieve the desired therapeutic effect.

The invention further provides use of the compounds of Formula (I) in the preparation of pharmaceutical medicament.

The antifungal activity of novel compounds of formula (I) (1Type-I or 2/Type-II) is summarized below in Table: 1 and Table: 2.

The following examples, which include preferred embodiments, will serve to illustrate the practice of this invention, it being understood that the particulars shown are by way of example and for purpose of illustrative discussion of preferred embodiments of the invention.

EXAMPLES

Example 1

Experimental Procedure for Synthesis of Alkynols (4, 7) and 2-azidophenols (5)

A. Mg (518 mg, 28.3 mmol) was flame dried in a two neck R. B. flask fitted with a reflux condenser and cooled to room temperature in argon atmosphere. Dry THF (30 mL) was introduced followed by a few crystals of iodine. Half of the total volume of n-BuCl (2.23 mL, 28.3 mmol) was added and the contents were refluxed till the generation of Grignard reagent. Heating was removed and rest of n-BuCl was added. Stirring was continued at room temperature till all the magnesium was consumed. Then the reaction mixture was cooled to 0° C. and acetylene gas was bubbled into it over 15 min. benzaldehyde (1.0 g, 9.4 mmol) in THF (20 mL) was added at 0° C. and stirred for 6 h. The reaction was quenched with saturated NH$_4$Cl solution, diluted with water, and extracted with ethyl acetate. The combined organic layers were dried over Na$_2$SO$_4$, concentrated and purified on silica gel (10% ethyl acctate in petroleum ether) to give 4 (1.08 g, 86%) as a yellowish oil.

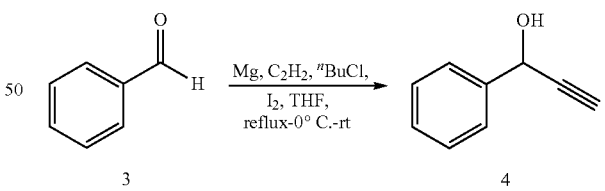

B. The amine 8 (1.0 eq.) was taken in 250 ml R. B. flask then water was added and it followed by HCl (6 eq.). To this mixture cold solution of NaNO$_2$ (1.0 eq.) was added at 0° C. and reaction was allowed for stirring for 30 min. The reaction mixture was became clear solution. The NaN$_3$ (1.0 eq.)was added slowly over 10 min and the reaction was allowed for stirring for 6 h at rt. The reaction mixture was diluted and extracted with EtOAc. The organic layer was dried over Na$_2$SO$_4$ and the solvents were evaporated under reduced pressure. The product (5) was purified by column chromatography.

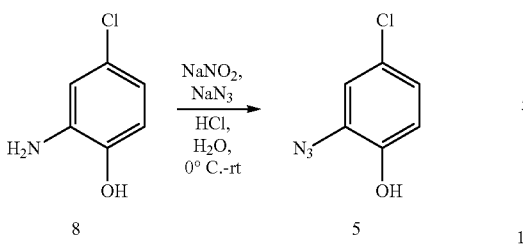

C. Zn (5.0 eq). propargyl bromide (3.0 eq), in THF was stirred vigorously for 30 min, to which a solution of ketone/aldehyde 6 (1.0 eq) in THF was added and the stirring was continued for another 30 min. The reaction mixture was cooled to 0° C. and saturated NH₄Cl was added drop wise for 30 min and stirring was continued overnight. Reaction mixture was filtered through Celite pad and the solvent was evaporated under vacuum and extracted with ethyl acetate, washed with brine, dried (Na₂SO₄), and concentrated. Purification of the crude by column chromatography (10% ethyl acetate in petroleum ether) afforded 7 (64%) as colorless syrup.

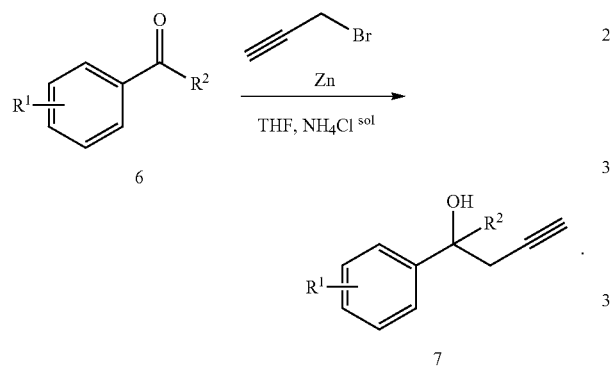

Example 2

Experimental Procedure for Synthesis of Triazole (1/Type I)

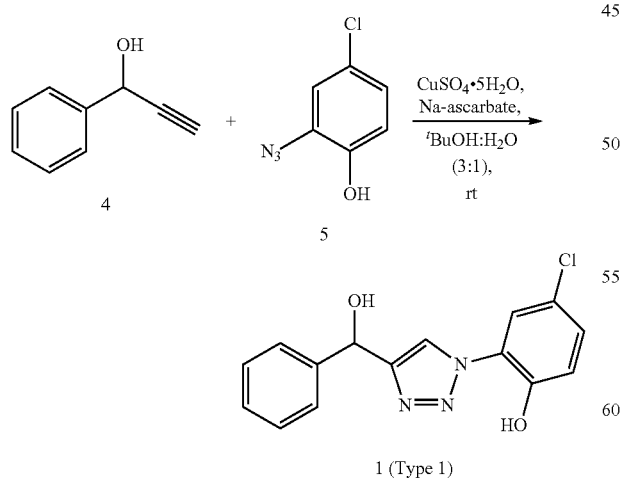

To a solution of azide 5 (1.0 eq.) and alkyne 4 (1.1 eq.) in $^t$BuOH:H₂O (3:1) at room temperature, sodium ascorbate (0.95 eq.) and CuSO₄ (0.2 eq.) were added and the resulting brick reddish mixture was stirred vigorously for 10 min. The reaction mixture was diluted and extracted with EtOAc. The organic layer was dried over Na₂SO₄ and the solvents were evaporated under reduced pressure. The product was purified by column chromatography.

Example 3

Experimental Procedure for Synthesis of Triazole (2/Type II)

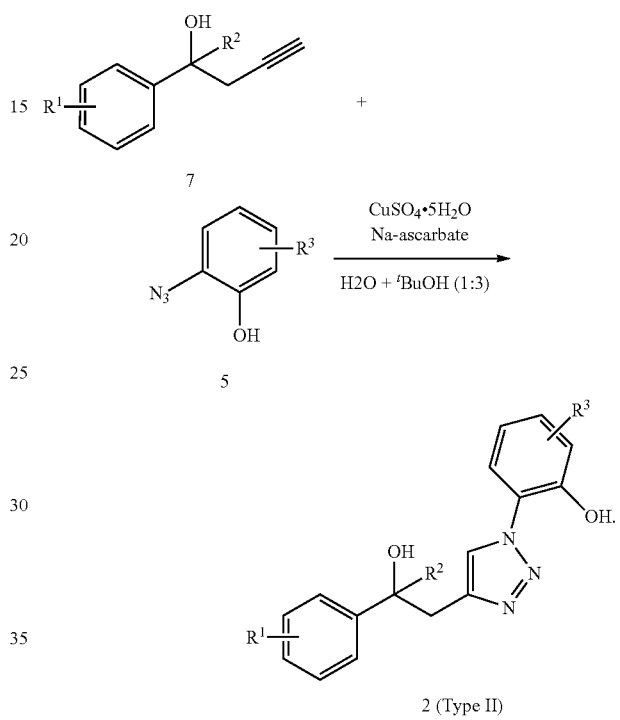

To a solution of azide 5 (1.0 eq.) and alkyne 7 (1.1 eq.) in $^t$BuOH: H₂O (3:1) at room temperature, sodium ascorbate (0.95 eq.) and CuSO₄ (0.2 eq.) were added and the resulting brick reddish mixture was stirred vigorously for 10 min. The reaction mixture was diluted and extracted with EtOAc. The organic layer was dried over Na₂SO₄ and the solvents were evaporated under reduced pressure. The product was purified by column chromatography.

Example 4

4-Chloro-2-(4-((3,5-dimethylphenyl)(hydroxy)methyl)-1H-1,2,3-triazol-1-yl)phenol (1aa)

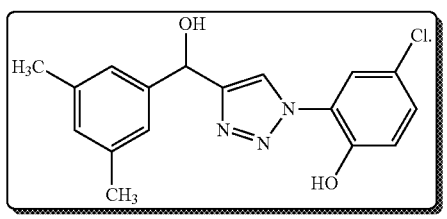

Isolated by column chromatography (pet.ether/AcOEt=6:4, $R_f$=0.3). The title compound was determined as colourless solid (86%). Mp: 191-193° C.; $^1$H NMR (200 MHz, CDCl₃):

δ 2.34 (s, 6H), 2.74 (d, J=3.5 Hz, 1H), 6.06 (d, J=2.9 Hz, 1H), 7.00 (s, 1H), 7.08-7.16 (m, 2H), 7.26 (dd, J=2.3, 8.8 Hz, 2H), 7.37 (d, J=2.4 Hz, 1H), 7.88 (s, 1H), 9.91 (s, 1H) ppm; $^{13}$C NMR (50 MHz, CDCl$_3$+MeOH (D$_4$)): δ 21.3 (q, 2C), 69.4 (d), 119.1 (d), 119.6 (d), 120.2 (d), 120.4 (d), 121.4 (s), 124.1 (d, 2C), 130.1 (d), 135.0 (s), 138.5 (s, 2C), 141.2 (s), 150.0 (s), 151.6 (s) ppm; IR(cm$^{-1}$): 3306, 3136, 2944, 1645, 1564, 1442, 1318, 1262, 1063, 875, 751, 669; HRMS(ESI) calcd for C$_{17}$H$_{17}$O$_2$N$_3$Cl(M$^+$+H): 330.1004; found: 330.1004.

Example 5

2-(4-((3,5-Bis(trifluoromethyl)phenyl)(hydroxy) methyl)-1H-1,2,3-triazol-1-yl)-4-chlorophenol (1ba)

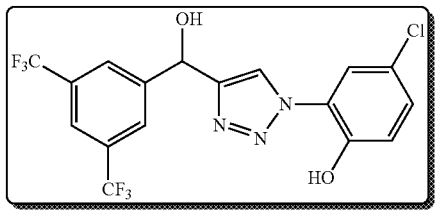

Isolated by column chromatography (pet.ether/ AcOEt=6.4, R$_f$=0.3). The title compound was determined as colourless solid (83%). Mp: 211-213° C.; $^1$H NMR (200 MHz, CDCl$_3$+MeOH (D$_4$)): δ 5.99 (s, 1H), 6.81 (d, J=8.7 Hz, 1H), 7.06 (dd, J=2.5, 8.7 Hz, 1H), 7.58 (d, J=2.5 Hz, 1H), 7.64 (bs, 1H), 7.86 (bs, 2H), 8.11 (s, 1H) ppm; $^{13}$C NMR (50 MHz, CDCl$_3$+MeOH (D$_4$)): δ 67.1 (d), 117.9 (d), 120.3 (s), 120.5 (d, t, J=3.7 Hz), 123.1 (d), 123.5 (d, 2C), 124.2 (s), 124.6 (s), 125.7 (s), 126.4 (d, J=1.8 Hz), 129.1 (d), 130.6 (s, d, J=33.3 Hz), 131.9 (s, d, J=33.7 Hz), 145.2 (s), 147.4 (s), 149.7 (s) ppm; IR(cm$^{-1}$): 3393, 3133, 2959, 1647, 1448, 1300, 1260, 876, 751, 724; HRMS(ESI) calcd for C$_{17}$H$_{11}$O$_2$N$_3$ClF$_6$ (M$^+$+H): 438.0439; found: 438.0445.

Example 6

4-chloro-2-(4-(2-hydroxy-2-phenylethyl)-1H-1,2,3-triazol-1-yl)phenol (1ea)

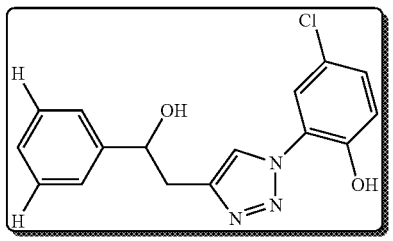

Isolated by column chromatography (pet.ether/AcOEt=6: 4, R$_f$=0.4). The title compound was determined as yellow solid (86%). Mp: 177-179° C.; $^1$H NMR (200 MHz, CDCl$_3$+ MeOH(D$_4$)): δ 0.73 (t, J=7.3 Hz, 3H), (m, 2H), 6.82 (d, J=8.8 Hz, 1H), (m, 4H), 7.32-7.43 (m, 2H), 7.55 (d, J=2.5 Hz, 1H), 8.05 (s, 1H) ppm; $^{13}$C NMR (50 MHz, CDCl$_3$+ MeOH (D$_4$)): δ 7.3 (q), 34.6 (t), 74.3 (s), 118.1 (d), 122.6 (d), 123.2 (d), 124.2 (s), 124.6 (s), 125.3 (d, 2C), 126.6 (d), 127.7 (d, 2C), 129.1 (d), 144.8 (s), 147.4 (s), 154.1 (s) ppm; IR(cm$^{-1}$): 3359, 3121, 2960, 1647, 1547, 1428, 1373, 1251, 1163, 966, 855, 754, 673; HRMS(ESI) calcd for C$_{17}$H$_{17}$O$_2$N$_3$Cl(M$^+$+H): 330.1004; found: 330.1007.

Example 7

5-Chloro-2-(4-((3,5-dimethylphenyl)(hydroxy) methyl)-1H-1,2,3-triazol-1-yl)phenol (1ab)

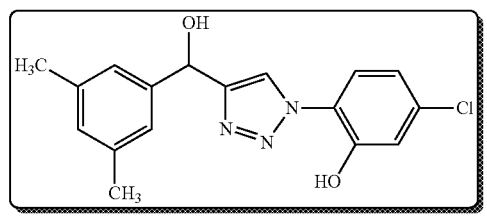

Isolated by column chromatography (pet.ether/AcOEt=6: 4, R$_f$=0.3). The title compound was determined as colourless solid (82%). Mp: 223-224° C.; $^1$H NMR (200 MHz, CDCl$_3$): δ 2.31 (s, 6H), 6.03 (s, 1H), 6.94 (d, J= 2.2, 8.7 Hz, 2H), 7.08 (s, 2H), 7.17 (d, J=2.3 Hz, 1H), 7.28 (d, J=8.6 Hz, 1H), 7.88 (s, 1H); $^{13}$C NMR (50 MHz, CDCl$_3$): δ 21.3 (q, 2C), 69.4 (d), 119.1 (d), 119.6 (d), 120.2 (d), 120.4 (d), 121.4 (s), 124.1 (d, 2C), 130.1 (d), 135.0 (s), 138.5 (s, 2C), 141.2 (s), 150.0 (s), 151.6 (s) ppm; IR (cm$^{-1}$): 3325, 3122, 2987, 2405, 1648, 1567, 1460, 1336, 1226, 1058, 874, 760, 664; HRMS (ESI) calcd for C$_{17}$H$_{17}$O$_2$N$_3$Cl(M$^+$+H): 330.1004; found: 330.1005.

Example 8

5-Chloro-2-(4-(1-hydroxy-1-phenylethyl)-1H-1,2,3-triazol-1-yl)phenol (2cb)

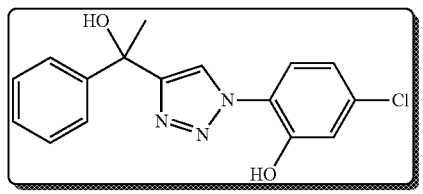

Isolated by column chromatography (pet.ether/AcOEt=6: 4, R$_f$=0.4). The title compound was determined as colourless solid (79%). Mp:232-234° C.; $^1$H NMR (200 MHz, CDCl$_3$+ MeOH (D$_4$)): δ 2.02 (s, 3H), 6.96 (dd, J=2.2, 8.6 Hz, 1H ), 7.07 (d, J=2.3 Hz, 1H), 7.22-7.36 (m, 3H), 7.50-7.56 (m, 2H), 7.63 (d J=8.6 Hz, 1H), 8.20 (s, 1H) ppm; $^{13}$C NMR (50 MHz, CDCl$_3$+MeOH (D$_4$)): δ 28.9 (q), 70.9 (s), 116.2 (d), 119.1 (d), 122.4 (d), 122.8 (s), 124.5 (d, 2C), 124.7 (d), 126.1 (d), 127.2 (d, 2C), 134.3 (s), 146.1 (s), 149.4 (s), 154.3 (s) ppm; IR(cm$^{-1}$): 3309, 3160, 2987, 1642, 1555, 1443, 1362, 1266, 1109, 1013, 975, 871, 753, 678; HRMS (ESI) calcd for C$_{16}$H$_{15}$O$_2$N$_3$Cl(M$^+$+H): 316.0847; found: 316.0846.

Example 9

4-Chloro-2-(4-(2-hydroxy-2-phenylethyl)-1H-1,2,3-triazol-1-yl)phenol (1ea)

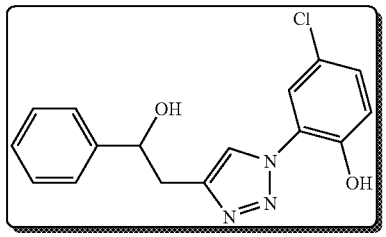

Isolated by column chromatography (pet.ether/AcOEt=6:4, $R_f$=0.3). The title compound was determined as colourless solid (83%). Mp: 148-150° C.; $^1$H NMR (200 MHz, CDCl$_3$+MeOH(D$_4$)): δ 3.22 (d, J=5.3 Hz, 2H), 5.04 (t, J=6.6 Hz, 1H), 7.03 (d, J=8.8 Hz, 1H), 7.22-7.43 (m, 6H), 7.71 (d, J=2.5 Hz, 1H), 8.08 (s, 1H) ppm; $^{13}$C NMR (50 MHz, CDCl$_3$+MeOH (D$_4$)) δ 34.8 (t), 72.5 (d), 117.7 (d), 123.3 (d), 123.8 (s), 123.9 (d), 124.6 (s), 125.3 (d, 2C), 126.9 (d), 127.8 (d, 2C), 129.0 (d), 143.2 (s), 143.7 (s), 147.4 (s) ppm; IR (cm$^{-1}$): 3363, 3131, 2998, 1643, 1552, 1314, 1253, 1044, 863, 764, 661; HRMS(ESI) calcd for C$_{16}$H$_{15}$O$_2$N$_3$Cl (M$^+$+H): 316.0847; found: 316.0847.

Example 10

5-Chloro-2-(4-(2-hydroxy-2-phenylethyl)-1H-1,2,3-triazol-1-yl)phenol (1eb)

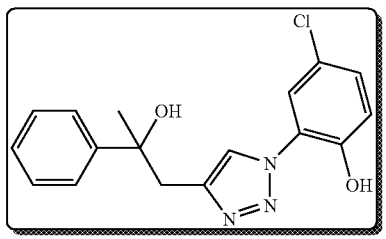

Isolated by column chromatography (pet.ether/AcOEt=6:4, $R_f$=0.3). The title compound was determined as colourless solid (83%). Mp: 171-172° C.; $^1$H NMR (200 MHz, CDCl$_3$+MeOH (D$_4$)) δ 3.19 (s, 2H), 5.01 (s, 1H), 6.95 (d, J=8.3 Hz, 1H), 7.06 (s, 1H), 7.25-7.36 (m, 5H), 7.58 (d, J=8.0 Hz, 1H), 8.01 (s, 1H) ppm; $^{13}$C NMR (50 MHz, CDCl$_3$+MeOH (D$_4$)) δ 34.7 (t), 72.4 (d), 116.4 (d), 119.3 (d), 122.9 (s), 124.7 (d), 125.2 (d, 2C), 126.8 (d), 127.6 (d, 3C), 134.4 (s, 2C), 143.2 (s), 149.5 (s) ppm; IR (cm$^{-1}$): 3341, 3142, 2972, 1651, 1563, 1324, 1221, 1063, 873, 750, 668; HRMS(ESI) calcd for C$_{16}$H$_{15}$O$_2$N$_3$Cl (M$^+$+H): 316.0847; found: 316.0854.

Example 11

4-Chloro-2-(4-(2-hydroxy-2-phenylpropyl)-1H-1,2,3-triazol-1-yl)phenol (2fa)

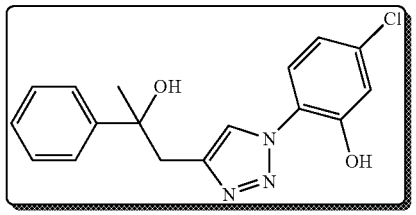

Isolated by column chromatography (pet.ether/AcOEt=6:4, $R_f$=0.4). The title compound was determined as colourless solid (79%). Mp: 180-181° C.; 1H NMR (200 MHz, CDCl$_3$+MeOH (D$_4$)) δ 1.61 (s, 3H), 3.28 (s, 2H), 6.98 (d, J=8.8 Hz, 1H), 7.20-7.37 (m, 4H), 7.43-7.49 (m, 2H), 7.65 (d, J=2.5 Hz, 1H), 7.83 (s, 1H) ppm; $^{13}$C NMR (50 MHz, CDCl$_3$+MeOH (D$_4$)) δ 27.9 (q), 39.5 (t), 73.0 (s), 117.6 (d), 123.3 (d), 123.7 (s), 124.3 (d, 3C), 124.5 (s), 126.0 (d), 127.4 (d, 2C), 128.9 (d), 142.9 (s), 146.7 (s), 147.4 (s) ppm; IR(cm$^{-1}$): 3344, 3067, 2950, 1942, 1736, 1645, 1598, 1437, 1303, 1233, 1158, 880, 748, 624; HRMS(ESI) calcd for C$_{17}$H$_{17}$O$_2$N$_3$Cl (M$^+$+H): 330.1004; found: 330.0999.

Example 12

5-Chloro-2-(4-(2-hydroxy-2-phenylpropyl)-1H-1,2,3-triazol-1-yl)phenol (2fb)

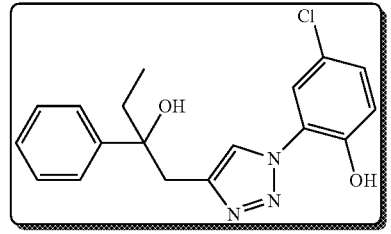

Isolated by column chromatography (pet.ether/AcOEt=6:4, $R_f$=0.4). The title compound was determined as colourless solid (83%). Mp: 189-190° C.; $^1$H NMR (200 MHz, CDCl$_3$+MeOH (D$_4$)) δ 1.61 (s, 3H), 3.28 (s, 2H), 6.95 (dd, J=2.3, 8.6 Hz, 1H), 7.05 (d, J=2.3 Hz, 1H), 7.22-7.36 (m, 3H), 7.44-7.49 (m, 2H), 7.55 (d, J=8.6 Hz, 1H), 7.76 (s, 1H) ppm; $^{13}$C NMR (50 MHz, CDCl$_3$+MeOH (D$_4$)): δ 28.2 (q). 39.6 (t), 73.1 (s), 116.6 (d), 119.4 (d), 122.9 (s), 124.4 (d, 3C), 124.7 (d), 126.1 (d), 127.5 (d, 2C), 134.5 (s), 142.9 (s), 146.7 (s), 149.6 (s) ppm; IR(cm$^{-1}$): 3448, 3162, 3022, 2929, 1643, 1552, 1445, 1364, 1263, 1155, 1006, 923, 874, 763; HRMS (ESI) calcd for C$_{17}$H$_{17}$O$_2$N$_3$Cl(M$^+$+H): 330.1004; found: 330.1009.

Example 13

4-Chloro-2-(4-(2-hydroxy-2-phenylbutyl)-1H-1,2,3-triazol-1-yl)phenol (2ga)

Isolated by column chromatography (pet.ether/AcOEt=6:4, $R_f$=0.4). The title compound was determined as colourless solid (85%). Mp: 153-155° C.; $^1$H NMR (400 MHz, CDCl$_3$+MeOH (D$_4$)): δ 0.80 (t, J=7.0 Hz, 3H), 1.85-2.02 (s, 1H), 3.32 (s, 2H), 6.97 (d, J=8.0 Hz, 1H), 7.18-7.22 (m, 2H), 7.31 (t, J=7.3 Hz, 2H), 7.37-7.42 (m, 2H), 7.57 (s, 1H), 7.71 (s, 1H) ppm; $^{13}$C NMR (50 MHz, CDCl$_3$+MeOH (D$_4$)): δ 7.5 (q), 34.7 (t), 38.4 (t), 76.5 (s), 118.7 (d), 122.8 (d), 123.4 (d), 124.4 (s, 2C), 125.3 (d, 2C), 126.4 (d), 127.9 (d, 2C), 129.4 (d), 143.5 (s), 144.7 (s), 147.7 (s) ppm; IR(cm$^{-1}$): 3329, 3173, 2953, 1632, 1558, 1 558, 1431, 1373, 1264, 1161, 971, 872, 748, 720, 683; HRMS(ESI) calcd for $C_{18}H_{19}O_2N_3Cl(M^++H)$: 344.1160; found: 344.1164.

Example 14

5-Chloro-2-(4-(2-hydroxy-2-phenylbutyl)-1H-1,2,3-triazol-1-yl)phenol (2gb)

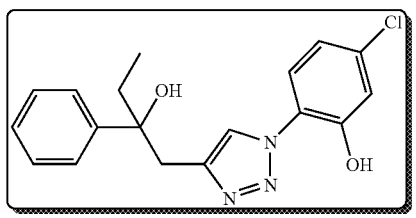

Isolated by column chromatography (pet.ether/AcOEt=6:4, $R_f$=0.4). The title compound was determined as yellow solid (80%). Mp: 129-131° C.; $^1$H NMR (400 MHz, CDCl$_3$+MeOH (D$_4$)): δ 0.79 (t, J=7.4 Hz, 3H), 1.83-2.05 (m, 2H), 3.32 (s, 2H), 6.88 (dd, J=8.5, 2.3 Hz, 1H), 7.05 (d, J=2.3 Hz, 1H), 7.18-7.22 (m, 1H), 7.28-7.34 (m, 3H), 7.38-7.40 (m, 2H), 7.57 (bs, 1H) ppm; $^{13}$C NMR (50 MHz, CDCl$_3$+MeOH (D$_4$)): δ 7.8 (q), 35.1 (t), 38.5 (t), 76.7 (s), 118.6 (d), 120.2 (d), 122.0 (d), 125.4 (d, 3C), 126.6 (d), 128.1 (d, 2C), 134.8 (s, 2C), 144.7 (s, 2C), 149.8 (s) ppm; IR(cm$^{-1}$): 3333, 3329, 2972, 1642, 1547, 1428, 1363, 1271, 1167, 971, 872, 747, 684; HRMS(ESI) calcd for $C_{18}H_{19}O_2N_3Cl(M^++H)$: 344.1161; found: 344.1164.

Example 15

4-chloro-2-(4-(2-hydroxy-2-phenylhexyl)-1H-1,2,3-triazol-1-yl)phenol (2ha)

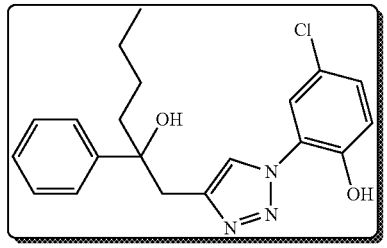

Isolated by column chromatography (pet.ether/AcOEt=6:4, $R_f$=0.5). The title compound was determined as colourless solid (86%). Mp: 165-167° C.; $^1$H NMR (400 MHz, CDCl$_3$+MeOH (D$_4$)): δ 0.83 (t, J=7.3 Hz, 3H), 1.01-1.11 (m, 1H), 1.20-1.36 (m, 3H), 1.81-1.89 (m, 1H), 1.91-1.99 (m, 1H), 3.32 (t, J=15.3 Hz, 1H), 4.03 (bs, 2H), 6.98 (d, J=8.8 Hz, 1H), 7.19-7.23 (m, 2H), 7.32 (t, J=7.8 Hz, 1H), 7.40 (d, J=7.5 Hz, 2H), 7.58 (d, J=2.3 Hz, 1H), 7.69 (s) ppm; $^{13}$C NMR (100 MHz, CDl$_3$+MeOH (D$_4$)): δ 13.4 (q), 22.6 (t), 25.2 (t), 38.7 (t), 41.7 (t), 76.0 (s), 118.2 (d), 123.2 (d), 123.9 (d), 124.1 (s), 124.6 (s), 125.1 (d, 2C), 126.1 (d), 127.7 (d, 2C), 129.2 (d), 143.2 (s), 145.0 (s), 147.6 (s) ppm; IR(cm$^{-1}$): 3459, 3116, 2980, 1639, 1547, 1334, 1231, 1056, 869, 750; HRMS(ESI) calcd for $C_{20}H_{23}O_2N_3Cl$ (M$^+$+H): 372.1473; found: 372.1471.

Example 16

4-Chloro-2-(4-(2-hydroxy-2,2-diphenylethyl)-1H-1,2,3-triazol-1-yl)phenol (2ia)

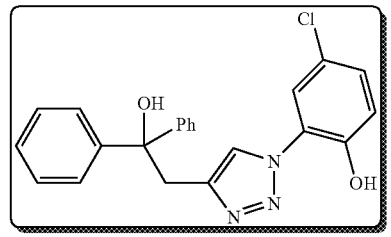

Isolated by column chromatography (pet.ether/AcOEt=7:3, $R_f$=0.5). The title compound was determined as colourless solid (83%). Mp: 194-196° C.; $^1$H NMR (200 MHz, CDCl$_3$+MeOH (D$_4$)): δ 3.82 (s, 2H), 6.96 (d, J=8.7 Hz, 1H), 7.17-7.35 (m, 7H), 7.46-7.51 (m, 6H), 7.58 (d, J=2.5 Hz, 1H), 7.66 (s, 1H) ppm; $^{13}$C NMR (50 MHz, CDCl$_3$+MeOH (D$_4$)): δ 37.9 (t), 77.2 (s), 118.0 (d), 123.3 (d), 124.0 (s), 124.2 (d), 124.5 (s), 125.8 (d, 4C), 126.5 (d, 2C), 127.6 (d, 4C), 129.1 (d), 143.1 (s), 146.0 (s, 2C), 147.5 (s) ppm; IR(cm$^{-1}$): 3355, 3173, 2988, 1637, 1529, 1435, 1263, 1152, 984, 873, 759, 620; HRMS(ESI) calcd for $C_{22}H_{19}O_2N_3Cl$ (M$^+$+H): 392.1160; found: 392.1162.

Example 17

5-Chloro-2-(-4-(2-hydroxy-2,2-diphenylethyl)-1H-1,2,3-triazol-1-yl)phenol (2ib)

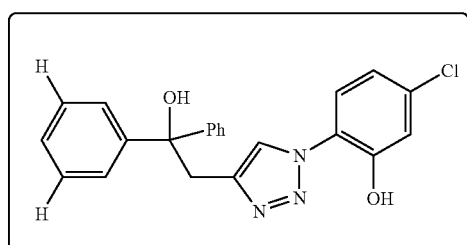

Isolated by column chromatography (pet.ether/AcOEt=7.3, $R_f$=0.5). The title compound was determined as colourless solid (81%). Mp: 210-212° C.; $^1$H NMR (200 MHz, CDCl$_3$+MeOH (D$_4$)): δ 3.81 (s, 2H), 6.89 (dd, J=2.2, 8.6 Hz, 1H), 7.02 (m, 1H), 7.15-7.33 (m, 6H), 7.38 (d, J=1.6 Hz, 1H), 7.43-7.50 (m, 4H). 7.54 (s, 1H) ppm; $^{13}$C NMR (50 MHz, CDCl$_3$+MeOH (D$_4$)): δ 38.0 (t), 77.2 (s), 117.3 (d), 119.8 (d), 122.8 (s), 123.9 (d), 124.2 (d), 125.9 (d, 4C), 126.7 (d, 2C), 127.8 (d, 4C), 134.7 (s), 143.2 (S) 146.0 (s. 2C). 149.7 (s) ppm; IR(cm$^{-1}$): 3321, 3137, 2970, 1639, 1598, 1543, 1437, 1323, 1236, 1152, 870, 740, 625; HRMS (ESI) calcd for $C_{22}H_{19}O_2N_3Cl$ (M$^+$+H): 392.1160; found: 392.1158.

Example 18

2-(-4-(2-(3,5-Bis(trifluoromethyl)phenyl)-2-hydroxyethyl)-1,2,3-triazol-1-yl)-4-chlorophenol (1ja)

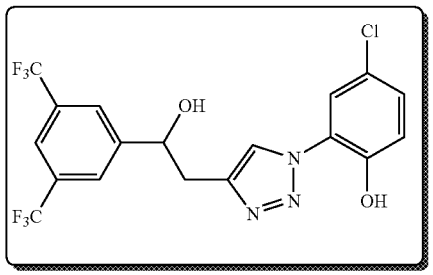

Isolated by column chromatography (pet.ether/AcOEt=6: 4, $R_f$=0.3). The title compound was determined as colourless solid (87%). Mp: 181-183° C.; $^1$H NMR (200 MHz, CDCl$_3$+MeOH (D$_4$)): δ 3.22 (d, J=6.4 Hz, 2H), 5.19 (t, J=6.4 Hz, 1H), 7.02 (d, J=8.8 Hz, 1H), 7.26 (dd, J=2.7, 8.6 Hz, 1H), 7.76 (d, J=2.7 Hz, 1H), 7.79 (bs, 2H), 7.90 (bs, 2H), 8.17 (s, 1H) ppm; $^{13}$C NMR (50 MHz, CDCl$_3$+MeOH (D$_4$)): δ 34.8 (t), 72.1 (d), 117.7 (d), 120.5 (s), 120.6 (d, J=4.0 Hz), 123.5 (d, 2C), 123.9 (s, 2C), 124.2 (d), 124.6 (s), 125.7 (d, J=2.9 Hz), 129.1 (d), 130.6 (s, d, J=33.3 Hz), 131.6 (s, d, J=33.3 Hz), 142.8 (s), 146.7 (s), 147.5 (s) ppm; IR(cm$^{-1}$): 3316, 3097, 2400, 1645, 1563, 1438, 1321, 1220, 1042, 867, 751, 660; HRMS(ESI) calcd for C$_{18}$H$_{13}$O$_2$N$_3$ClF$_6$ (M$^+$+H): 452.0595; found: 452.0600.

Example 19

2-(4-(2-(3,5-Bis(trifluoromethyl)phenyl)-2-hydroxyethyl)-1H-1,2,3-triazol-1-yl)-5-chlorophenol (1jb)

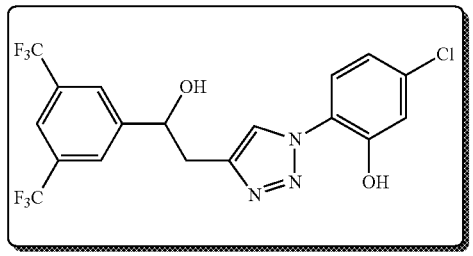

Isolated by column chromatography (pet.ether/AcOEt=6: 4, $R_f$=0.3). The title compound was determined as colourless solid (82%). Mp: 192-194° C.; $^1$H NMR (200 MHz, CDCl$_3$+MeOH (D$_4$)): δ 3.21 (d, J=6.4 Hz, 2H), 5.19 (t, J=6.3 Hz, 1H), 6.98 (dd, J=2.2, 8.6 Hz, 1H), 7.08 (d, J=2.2 Hz, 1H), 7.60 (d, J=8.6 Hz, 1H), 7.79 (bs, 2H), 7.88 (bs, 2H), 8.09 (bs, 1H) ppm; $^{13}$C NMR (50 MHz, CDCl$_3$+MeOH (D$_4$)): δ 34.9 (t), 71.2 (d), 116.7 (d), 119.6 (d, 2C), 120.3 (s), 120.6 (d, t, J=3.3 Hz), 122.9 (s), 124.8 (d, 2C), 125.8 (d, J=3.3 Hz), 130.3 (s, d, J=33.3 Hz ), 131.6 (s, d, J=32.9 Hz), 134.7 (s, 2C), 146.7 (s, 2C), 149.7 (s) ppm; IR(cm$^{-1}$): 3298, 3161, 2984, 1645, 1599, 1443, 1309, 1211, 1095, 871, 757, 682; HRMS(ESI) calcd for C$_{18}$H$_{13}$O$_2$N$_3$ClF$_6$ (M$^+$+H): 452.0595; found: 452.0599.

Example 20

2-(4-(2-(3,5-Bis(trifluoromethyl)phenyl)-2-hydroxypropyl)-1H-1,2,3-triazol-1-yl)-4-chlorophenol (2sa)

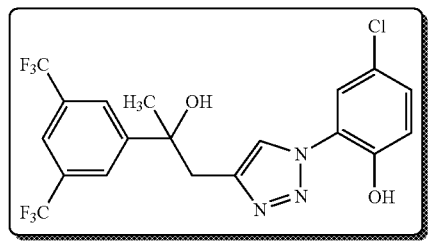

Isolated by column chromatography (pet.ether/AcOEt=6: 4, $R_f$=0.4). The title compound was determined as colourless solid (85%). Mp: 1642-166° C.; $^1$H NMR (200 MHz, CDCl$_3$+MeOH (D$_4$)): δ 1.67 (s, 3H), 3.30 (s, 2H), 7.00 (d, J=8.8 Hz, 1H), 7.24 (dd, J=2.5, 8.8 Hz, 1H), 7.69 (d, J=2.5 Hz, 1H), 7.76 (bs, 1H), 7.97 (s, 2H), 8.08 (s, 1H) ppm; $^{13}$C NMR (50 MHz, CDCl$_3$+MeOH (D$_4$)): δ 28.1 (q), 39.4 (t), 72.7 (s), 117.7 (d), 119.9 (d, J=4.0 Hz), 120.3 (s), 123.4 (d, 2C), 123.9 (s, 2C), 124.5 (d), 125.1 (d, d, J=2.9 Hz), 125.7 (s), 129.1 (d), 130.7 (s, d, J=32.9 Hz), 143.2 (s, 2C), 147.7 (s) 150.3 (s) ppm; IR(cm$^{-1}$): 3453, 3152, 2993, 1640, 1600, 1555, 1437, 1363, 1248, 1160, 1023, 983, 871, 764; HRMS(ESI) calcd for C$_{19}$H$_{15}$O$_2$N$_3$ClF$_6$ (M$^+$+H): 466.00752; found: 466.0755.

Example 21

2-(4-(2-(3,5-Bis(trifluoromethyl)phenyl)-2-hydroxypropyl)-1H-1,2,3-triazol-1-yl)-5-chlorophenol (2sb)

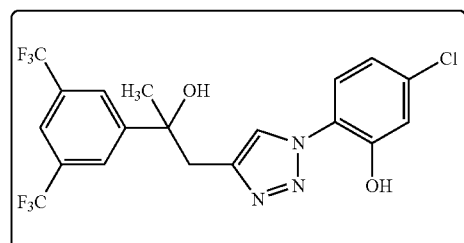

Isolated by column chromatography (pet.ether/AcOEt=6: 4, $R_f$=0.4). The title compound was determined as colourless solid (80%). Mp: 156-158° C.; $^1$H NMR (200 MHz, CDCl$_3$MeOH (D$_4$)): δ 1.68 (s, 3H), 3.29 (s, 2H), 6.96 (dd, J=2.2, 8.6 Hz, 1H), 7.07 (d, J=2.2, 1H), 7.58 (d, J=8.6 Hz, 1H), 7.76 (bs, 1H), 7.97 (s, 2H), 8.01 (s, 1H) ppm; $^{13}$C NMR (50 MHz, CDCl$_3$+MeOH (D$_4$)): δ 28.1 (q), 39.4 (t), 72.8 (s), 116.6 (d), 119.4 (d), 119.9 (d, J=4.0 Hz), 120.3 (s), 122.9 (s), 124.6 (d), 124.8 (d, 2C), 125.1 (d, d, J=2.9 Hz), 125.7 (s), 130.1 (s, d, J=32.9 Hz), 131.4 (s, d, J=32.9 Hz), 134.6 (s), 142.2 (s), 149.6 (s), 150.2 (s) ppm; IR(cm$^{-1}$): 3322, 3129, 2983, 1633, 1600, 1535, 1427, 1363, 1248, 1170, 1027, 989, 878, 754; HRMS(ESI) calcd for C$_{19}$H$_{15}$O$_2$N$_3$ClF$_6$ (M$^+$+H): 466.00752; found: 466.0750.

Example 22

4-Chloro-2-(4-(2-(2,4-difluorophenyl)-2-hydroxypropyl)-1H-1,2,3-triazol-1-yl)phenol (2ka)

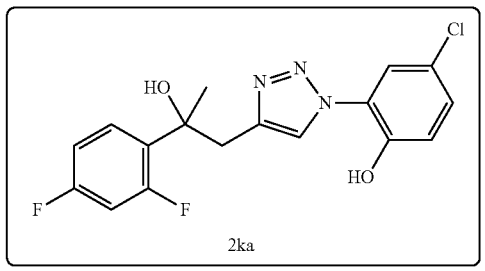 [SMILES: CC(O)(Cc1cn(-c2cc(Cl)ccc2O)nn1)c1ccc(F)cc1F]

Brown color solid; 82%; ($R_f$=0.3, 30% ethyl acetate/pet. ether); $^1$H NMR (200 MHz, {MeOD+CDCl$_3$}): δ 1.60 (d, J=1.0 Hz, 3H), 3.26 (d, J=14.9 Hz, 1H), 3.44 (d, J=14.8 Hz, 1H), 6.64-6.78 (m, 2H), 6.93 (d, J=8.8 Hz, 1H), 7.15 (dd, J=8.8, 2.5 Hz, 1H), 7.40-7.54 (m, 2H), 7.76 (s, 1H); $^{13}$C NMR (125 MHz, {MeOD+CDCl$_3$}): δ 27.4 (q), 37.4 (t), 72.1 (s), 103.5 (dd, J=25.7, 27.7 Hz), 110.1 (dd, J=2.9, 20.0 Hz), 117.8 (d), 123.2 (d), 124.0 (s), 124.1 (d), 124.6 (s), 128.2 (dd, J=6.5, 9.5 Hz), 129.0 (d), 129.3 (s), 143.0 (s), 147.4 (s), 157.8 (s), 159.8 (s), 160.7 (s), 162.6 (s) ppm; HRMS(ESI+): calcd. For C$_{17}$H$_{14}$ClF$_2$N$_3$O$_2$ [M+H]$^+$ 365.0743; found 366.0816.

Example 23

4-Chloro-2-(4-(2-(2,4-dichlorophenyl)-2-hydroxypropyl)-1H-1,2,3-triazol-1-yl)phenol (2 ma)

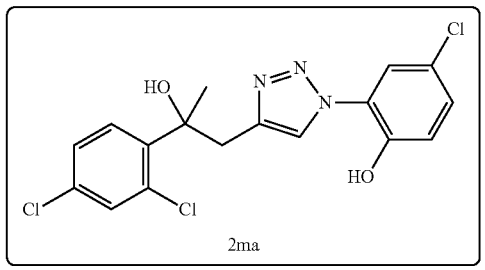 [SMILES: CC(O)(Cc1cn(-c2cc(Cl)ccc2O)nn1)c1ccc(Cl)cc1Cl]

Orange color solid; 81%; ($R_f$=0.3, 30% ethyl acetate/pet. ether); $^1$H NMR (500 MHz, {MeOD+CDCl$_3$}): δ 1.92 (s, 3H), 3.64 (d, J=14.9 Hz, 1H, 3.87 (d, J=14.9 Hz, 1H), 7.10 (dd, J=8.9, 2.1 Hz, 1H), 7.20 (d, J=2.1 Hz, 1H), 7.35 (dd, j=8.5, 2.1 Hz, 1H), 7.53 (d, J=2.1 Hz, 1H), 7.71 (d, J=8.5 Hz, 1H), 7.86 (d, J=8.5 Hz, 1H), 8.09 (br. s., 1H); $^{13}$C NMR (125 MHz, {MeOD+CDCl$_3$}): δ 26.1 (q), 35.7 (t), 73.4 (s), 116.5 (d), 119.3 (d), 122.9 (s), 124.6 (d), 126.2 (d), 128.9 (d), 129.9 (d), 130.7 (s), 132.6 (s), 134.4 (s), 142.0 (s), 149.5 (s) ppm; HRMS (ESI+): calcd. For C$_{17}$H$_{14}$Cl$_3$N$_3$O$_2$ [M+H]$^+$ 397.0152; found 398.0224.

Example 24

4-Chloro-2-(4-(2-(4-(dimethylamino)phenyl)-2-hydroxyethyl)-1H-1,2,3-triazol-1-yl)phenol (2pa)

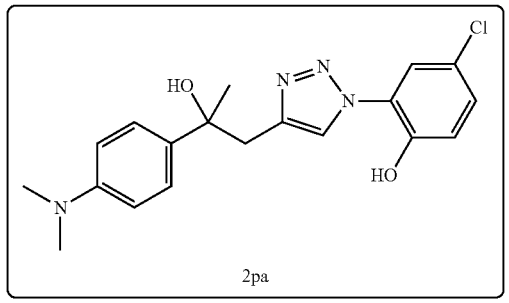 [SMILES: CN(C)c1ccc(C(C)(O)Cc2cn(-c3cc(Cl)ccc3O)nn2)cc1]

Brown color solid; 84%; ($R_f$=0.3, 35% ethyl acetate/pet. ether); $^1$H NMR (200 MHz, {MeOD+CDCl$_3$}): δ 3.28 (s, 6H), 3.51-3.59 (m, 2H), 5.22-5.34 (m, 1H), 7.11 (d, J=8.8 Hz, 2H), 7.35 (d, J=8.7 Hz, 1H), 7.56 (d, J=2.5 Hz, 1H), 7.58-7.61 (m, 1H), 7.62 (d, J=3.4 Hz, 1H), 8.02 (d, J=2.4 Hz, 1H), 8.37 (s, 1H); $^{13}$C NMR (125 MHz, {MeOD+CDCl$_3$}): δ 35.0 (t), 40.6 (q, 2C), 72.6 (s), 112.7 (d, 2C), 118.8 (d), 122.6 (d), 123.0 (s), 124.5 (s), 126.7 (d, 2C), 127.5 (d), 129.3 (d), 147.7 (s), 150.1 (s) ppm; HRMS (ESI+): calcd. For C$_{18}$H$_{19}$ClN$_4$O$_2$[M-H$_2$O]$^+$ 358.1197; found 341.1159.

Example 25

5-Chloro-2-(4-(2-(2,4-difluorophenyl)-2-hydroxypropyl)-1H-1,2,3-triazol-1-yl)phenol (2kb)

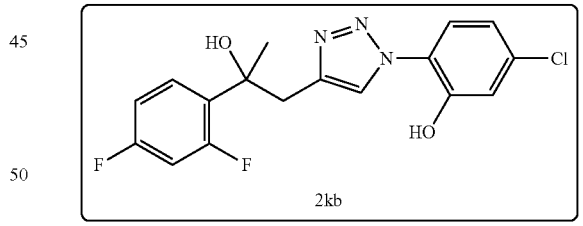

Brown color solid; 81%; ($R_f$=0.3, 30% ethyl acetate/pet. ether); $^1$H NMR (500 MHz, {MeOD+CDCl$_3$}): δ 1.59 (s, 3H), 3.26 (d, J=14.9 Hz, 1H), 3.41 (d, J=14.9 Hz, 1H), 6.65-6.74 (m, 2H), 6.85 (dd, J=8.6, 2.1 Hz, 1H), 6.98 (d, J=1.9 Hz, 1H), 7.38 (d, J=8.4 Hz, 1H), 7.42-7.49 (m, 1H), 7.73 (s, 1H) ppm; $^{13}$C NMR (125 MHz, {MeOD+CDCl$_3$}): δ 28.2 (q), 37.4 (t), 72.8 (s), 103.7 (s), 103.9 (dd, J=26.1, 27.7 Hz), 110.6 (s), 110.7 (dd, J=3.4, 20.20 Hz), 117.8 (d), 120.1 (d), 122.6 (s), 123.0 (d), 123.6 (d), 128.5 (s), 134.8 (s), 143.6 (s), 149.7 (s), 157.9 (s), 159.8 (s), 160.9 (s), 162.9 (s) ppm; HRMS (ESI+): calcd. For C$_{17}$H$_{14}$ClF$_2$N$_3$O$_2$ [M+H]$^+$ 365.0743; found 366.0814.

Example 26

5-Chloro-2-(4-(2-(2,4-dichlorophenyl)-2-hydroxy-propyl)-1H-1,2,3-triazol-1-yl)phenol (2mb)

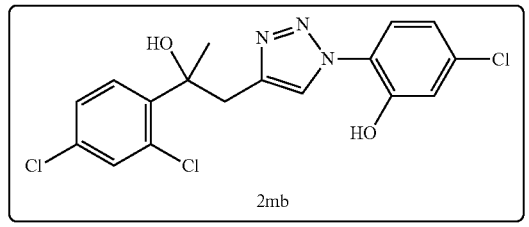 [SMILES: CC(O)(Cc1cn(-c2ccc(Cl)cc2O)nn1)c1ccc(Cl)cc1Cl]

Orange color solid; 83%; ($R_f$=0.3, 30% ethyl acetate/pet.ether); $^1$H NMR (400 MHz, {MeOD+CDCl$_3$}): δ 1.68 (s, 3H), 3.34 (d, J=15.1 Hz, 1H), 3.78 (d, J=14.7 Hz, 1H), 6.9 (dd, J=8.7, 2.3 Hz, 1H), 6.97 (d, J=2.3 Hz, 1H), 7.09 (dd, J=8.7, 2.3 Hz, 1H), 7.26 (d, J=2.3 Hz, 1H), 7.37 (d, J=8.7 Hz, 1H), 7.61 (d, J=8.7 Hz, 1H), 7.71 (s, 1H); $^{13}$C NMR (100 MHz, {MeOD+CDCl$_3$}): δ 27.0 (q), 35.9 (t), 74.3 (s), 117.8 (d), 120.1 (d), 122.7 (s), 123.6 (d), 126.9 (d), 129.4 (d), 130.5 (d), 130.9 (s), 133.2 (s), 134.8 (s), 142.0 (s), 149.7 (s) ppm; HRMS (ESI+): calcd. For C$_{17}$H$_{14}$Cl$_3$N$_3$O$_2$ [M+]$^+$ 397.0152; found 398.0225.

Example 27

5-Chloro-2-(4-(2-(2-fluoro-4-(trifluoromethyl)phenyl)-2-hydroxyethyl)-1H-1,2,3-triazol-1-yl)phenol (2ob)

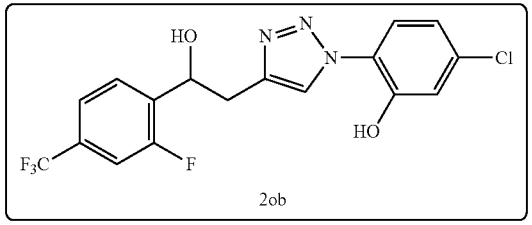 [SMILES: Oc1cc(Cl)ccc1-n1cc(CC(O)c2ccc(C(F)(F)F)cc2F)nn1]

Brown color solid; 83%; ($R_f$=0.3, 35% ethyl acetate/pet. ether); $^1$H NMR (400 MHz, {MeOD+CDCl$_3$}): δ 3.0 (d, J=8.3 Hz, 1H), 3.07-3.16 (m, 1H), 4.92 (br. s., 1H), 5.24 (br. s., 1H), 6.76-6.82 (m, 1H), 6.95-7.00 (m, 1H), 7.13 (d, J=9.8 Hz, 1H), 7.28 (br. s., 1H), 7.45 (dd, J=8.7, 2.8 Hz, 1H), 7.55-7.62 (m, 1H), 7.94 (br. s., 1H), 10.06 (br. s., 1H); $^{13}$C NMR (100 MHz, {MeOD+CDCl}): δ 29.3 (q), 33.9 (t), 66.1 (d), 112.2 (d, J=24.6 Hz), 117.5 (d), 119.7 (d), 120.7 (d), 123.1 (s), 123.3 (s), 124.2 (d), 128.1 (d), 128.2 (s), 134.3 (s), 149.6 (s), 157.4 (s), 159.9 (s) ppm; HRMS (ESI+): calcd. For C$_{17}$H$_{12}$ClF$_4$N$_3$O$_2$ [M+H]$^+$ 401.0554; found 402.0621.

Example 28

2-(4-(2-(2,4-Difluorophenyl)-2-hydroxypropyl)-1H-1,2,3-triazol-1-yl)-5-fluorophenol (2kc)

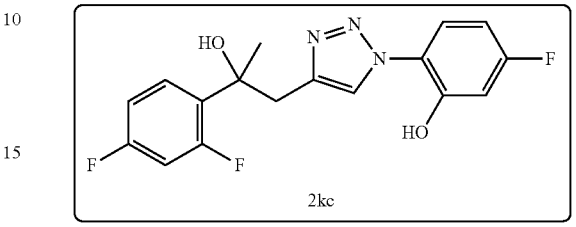

Brown color solid; 81%; ($R_f$=0.3, 35% ethyl acetate/pet. ether); $^1$H NMR (200 MHz, {MeOD+CDCl$_3$}): δ 1.66 (s, 3H), 3.33 (d, J=14.9 Hz, 1H), 3.52 (d, J=14.9 Hz, 1H), 6.64-6.86 (m, 2H), 6.88-7.09 (m, 2H), 7.14-7.36 (m, 1H), 7.40-7.65 (m, 1H), 7.85 (s, 1H); $^{13}$C NMR (50 MHz, {MeOD+CDCl$_3$}): δ 28.4 (q), 37.4 (t), 72.8 (s), 104.0 (dd, J=25.3, 27.4 Hz), 108.3 (d), 108.8 (d), 110.8 (dd, J=3.3, 20.5 Hz), 116.0 (d), 116.4 (d), 119.1 (d, J=8.42 Hz), 122.2 (d), 128.6 (dd, J=6.2, 9.5 Hz), 129.4 (s), 143.9 (s), 145.0 (s), 153.4 (s), 158.2 (s) ppm; HRMS (ESI+): calcd. For C$_{17}$H$_{14}$F$_3$N$_3$O$_2$ [M+H]$^+$ 349.1038; found 350.1104.

Example 29

2-(4-(2-(2,4-Dichlorophenyl)-2-hydroxypropyl)-1H-1,2,3-triazol-1-yl)-5-fluorophenol (2mc)

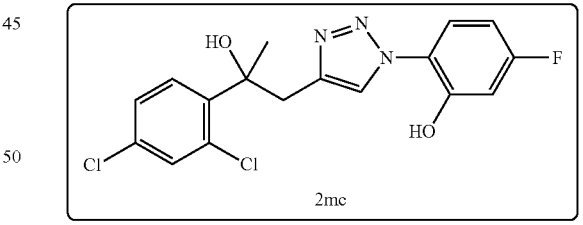

Orange color solid; 86%; ($R_f$=0.3, 30% ethyl acetate/pet. ether); $^1$H NMR (200 MHz, {MeOD+CDCl$_3$}): δ 2.3 (s, 3H), 4.03 (d, J=15.0 Hz, 1H), 4.36 (d, J=15.0 Hz, 1H), 7.50-7.58 (m, 2H), 7.74 (dd, J=8.6, 2.3 Hz, 1H), 7.88-8.00 (m, 2H), 8.26 (d, J=8.6 Hz, 1H), 8.6 (s, 1H); $^{13}$C NMR (50 MHz, {MeOD+CDCl$_3$}): δ 26.6 (q), 35.9 (t), 73.9 (s), 109.7 (d), 110.2 (d), 115.6 (d), 116.1 (d), 117.9 (d, J=8.4 Hz, ), 123.7 (d), 126.6 (d), 129.1 (d), 130.3 (d), 130.9 (s), 132.9 (s), 142.0 (s), 143.2 (s), 144.8 (s), 153.1 (s), 157.9 (s) ppm; HRMS (ESI+): calcd. For C$_{17}$H$_{14}$F$_3$N$_3$O$_2$ [M+H]$^+$ 381.0447; found 382.0515.

Example 30

5-Fluoro-2-(4-(2-(2-fluoro-4-(trifluoromethyl)phenyl)-2-hydroxyethyl)-1H-1,2,3-triazol-1-yl)phenol (2oc)

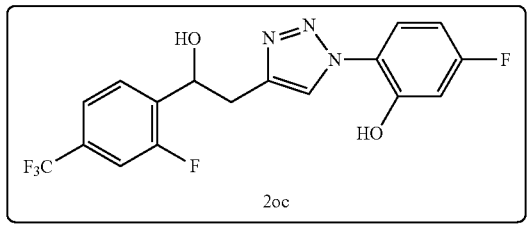 [SMILES: Oc1cc(F)ccc1-n1cc(CC(O)c2ccc(C(F)(F)F)cc2F)nn1]

Brown color solid; 79%; ($R_f$=0.3, 35% ethyl acetate/pet. ether); $^1$H NMR (500 MHz, {MeOD+CDCl$_3$}): δ 3.12 (dd, J=8.2, 14.9 Hz, 1H), 3.15 (dd, J=4.3, 14.9 Hz, 1H), 5.26 (dd, J=4.3, 7.9 Hz, 1H), 6.96 (d, J=2.6 Hz, 1H), 6.90 (d, J=2.0 Hz, 1H), 7.26 (d, J=10.1 Hz, 1H), 7.32 (br. s., 2H), 7.39-7.41 (m, 2H), 7.64 (t, J=7.6 Hz, 1H), 8.09 (s, 1H); $^{13}$C NMR (125 MHz, {MeOD+CDCl$_3$}): δ 33.4 (t), 65.0 (d), 109.9 (d), 110.2 (d), 112.5 (d), 116.0 (d), 116.2 (d), 118.1 (d, J=9.1 Hz), 121.0 (t, J=3.6 Hz), 123.5 (d), 128.1 (d, J=4.5 Hz, 1C), 135.0 (s), 143.5 (s), 144.9 (s), 154.7 (s), 156.6 (s), 157.9 (s), 159.9 (s) ppm; HRMS (ESI+): calcd. For $C_{17}H_{12}F_5N_3O_2$ [M+H]$^+$ 385.0850; found 386.0917.

Example 31

5-Fluoro-2-(4-(2-(4-fluorophenyl)-2-hydroxypropyl)-1H-1,2,3-triazol-1-yl)phenol (2qc)

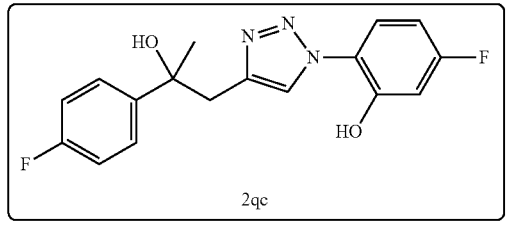 [SMILES: CC(O)(Cc1cn(-c2ccc(F)cc2O)nn1)c1ccc(F)cc1]

Brown color solid; 83%; ($R_f$=0.3, 30% ethyl acetate/pet. ether); $^1$H NMR (500 MHz, {MeOD+CDCl$_3$}): δ 1.54 (s, 3H), 3.21 (s, 2H), 6.87-7.00 (m, 4H), 7.29 (s, 1H), 7.32-7.42 (m, 2H), 7.76 (s, 1H); $^{13}$C NMR (125 MHz, {MeOD+CDCl$_3$}): δ 29.3 (q), 39.9 (t), 73.4 (s), 109.7 (dd, J=27.7 Hz), 114.6 (dd, J=21.0 Hz, 2C), 116.1 (dd, J=22.9 Hz), 118.3 (dd, J=8.6 Hz), 123.5 (d), 126.5 (dd, J=8.6 Hz, 2C), 142.8 (s), 144.9 (s), 154.7 (s), 156.6 (s), 160.5 (s), 162.5 (s) ppm; HRMS (ESI+): calcd. For $C_{17}H_{15}F_2N_3O_2$ [M+H]$^+$ 331.1132; found 332.1199.

Example 32

2-(4-(2-(4-Chlorophenyl)-2-hydroxypropyl)-1H-1,2,3-triazol-1-yl)-5-fluorophenol (2lc)

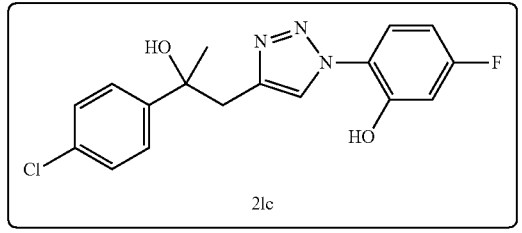 [SMILES: CC(O)(Cc1cn(-c2ccc(F)cc2O)nn1)c1ccc(Cl)cc1]

Light orange color solid; 82%; ($R_f$=0.3, 30% ethyl acetate/pet. ether); $^1$H NMR (200 MHz, {MeOD+CDCl$_3$}): δ 1.53 (s, 3H), 3.20 (s, 2H), 6.94 (d, J=5.8 Hz, 2H), 7.30 (s, 2H), 7.25 (s, 1H), 7.31-7.38 (m, 2H), 7.80 (s, 1H); $^{13}$C NMR (125 MHz, {MeOD+CDCl$_3$}): δ 29.6 (q), 39.7 (t), 73.5 (s), 109.2 (m, 1C), 116.1 (d, J=22.7 Hz), 118.7 (d, J=8.2 Hz), 122.9 (d), 123.6 (s), 126.3 (d, 2C), 128.1 (d, 2C), 132.4 (s), 143.6 (s), 145.0 (s), 145.7 (s), 154.8 (s) ppm; HRMS (ESI+): calcd. For $C_{17}H_{15}ClFN_3O_2$ [M+H]$^+$ 347.0837; found 348.0903.

Example 33

2-(4-(2-(4-Bromophenyl)-2-hydroxypropyl)-1H-1,2,3-triazol-1-yl)-5-fluorophenol (2nc)

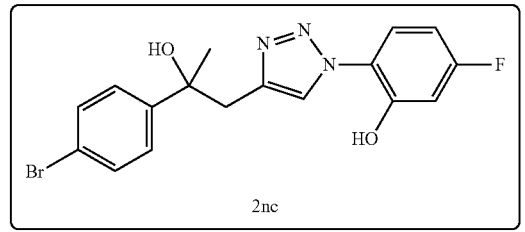 [SMILES: CC(O)(Cc1cn(-c2ccc(F)cc2O)nn1)c1ccc(Br)cc1]

Brown color solid; 83%; ($R_f$=0.3, 30% ethyl acetate/pet.ether); $^1$H NMR (200 MHz, {MeOD+CDCl$_3$}): δ 1.63 (s, 3H), 3.32 (d, J=1.6 Hz, 2H), 6.97-7.06 (m, 2H), 7.10-7.17 (m, 1H), 7.30-7.38 (m, 2H), 7.41-7.49 (m, 2H), 7.68 (s, 1H), 9.62 (s, 1H); $^{13}$C NMR (50 MHz, {MeOD+CDCl$_3$}): δ 29.4 (q), 39.6 (t), 73.5 (s), 109.1 (d), 109.6 (d), 115.9 (d), 116.4 (d), 118.5 (dd, J=8.8 Hz), 120.5 (s), 123.1 (d), 126.7 (d, 2C), 131.1 (d, 2C), 143.5 (s), 146.2 (s) ppm; HRMS (ESI+): calcd. For $C_{17}H_{15}BrFN_3O_2$ [M+H]$^+$ 391.0332; found 392.0398.

Example 34

4-Chloro-2-(4-(2-(4fluorophenyl)-2-hydroxypropyl)-1H-1,2,3-triazol-1-yl)phenol (2qa)

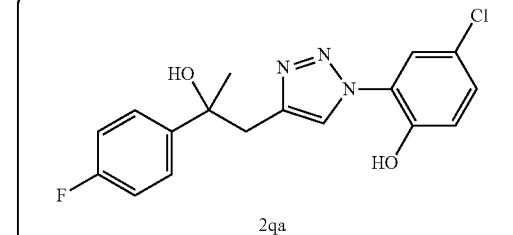

Brown color solid; 79%; (R$_f$=0.3, 30% ethyl acetate/pet. ether); $^1$H NMR (200 MHz, {MeOD+CDCl$_3$}): δ 1.6 (s, 3H), 3.21 (s, 2H), 6.90-6.99 (m, 3H) 7.17 (dd, J=8.8, 2.5 Hz, 1H), 7.33-7.42 (m, 2H), 7.59 (d, J=2.5 Hz, 1H), 7.77 (s, 1H); $^{13}$C NMR (50 MHz, {MeOD+CDCl$_3$}): δ 29.0 (q), 39.9 (t), 73.3 (s), 114.2 (d), 114.7(d), 118.3 (d), 123.1 (d), 124.3 (s), 126.4 (d, 2C), 126.5 (d, 2C), 129.3 (d, 2C). 142.7 (s). 147.5 (s) ppm; HRMS (ESI+): calcd. For C$_{17}$H$_{15}$ClFN$_3$O$_2$ [M+H]$^+$ 347.0837; found 348.0904.

Example 35

4-Chloro-2-(4-(2-(4-chlorophenyl)-2-hydroxypropyl)-1H-1,2,3-triazol-1-yl)phenol (2la)

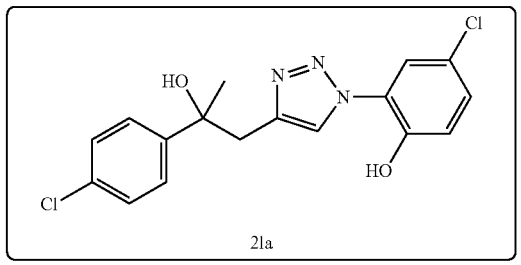 [SMILES: CC(O)(Cc1cn(-c2cc(Cl)ccc2O)nn1)c1ccc(Cl)cc1]

Orange color solid; 82%; (R$_f$=0.3, 30% ethyl acetate/pet. ether); $^1$H NMR (400 MHz, {MeOD+CDCl$_3$}): δ 1.54 (s, 3H), 3.21 (s, 2H), 6.94 (d, J=8.8 Hz, 1H), 7.17 (dd, J=8.6, 2.5 Hz, 1H), 7.23 (d, J=8.6 Hz, 2H), 7.32-7.38 (m, 3H), 7.59 (d, J=2.5 Hz, 1H), 7.81 (br. s., 1H); $^{13}$C NMR (101 MHz, {MeOD+CDCl$_3$}): δ 29.0 (q), 39.6 (t), 73.3 (s), 118.3 (d) 123.2 (d) 123.9 (s), 124.3 (s), 124.6 (s), 126.3 (d, 2C). 127.9 d, 3C), 129.3 (d), 132.2 (s), 145.6 (s), 147.6 (s) ppm; HRMS (ESI$^+$): calcd. For C$_{17}$H$_{15}$Cl$_2$N$_3$O$_2$ [M+H]$^+$ 363.0541: found 364.0809.

Example 36

2-(4-(2-(4-Bromophenyl)-2-hydroxypropyl)-1H-1,2,3-triazol-1-yl)-4-chlorophenol (2na)

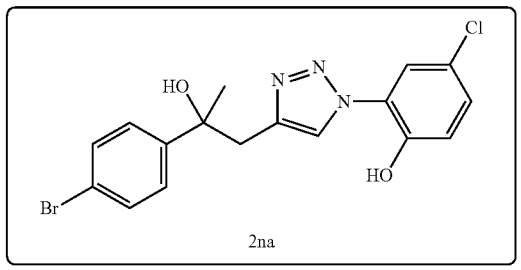 [SMILES: CC(O)(Cc1cn(-c2cc(Cl)ccc2O)nn1)c1ccc(Br)cc1]

Brown color solid; 83%; (R$_f$=0.3, 30% ethyl acetate/pet. ether); $^1$H NMR (200 MHz, {MeOD+CDCl$_3$}): δ 1.52 (s, 3H), 3.20 (s, 2H), 6.93 (d, J=8.8 Hz, 1H), 7.11-7.42 (m, 5H), 7.52 (d, J=2.5 Hz, 1H), 7.77 (s, 1H); $^{13}$C NMR (50 MHz, {MeOD+CDCl$_3$}): δ 29.3 (q), 39.6 (t), 73.5 (s), 118.8 (d), 120.5 (s), 122.7 (d), 123.4 (d), 124.4 (s), 124.5 (s), 126.7 (d, 2C), 129.4 (d), 131.0 (d, 2C), 146.2 (s, 2C), 147.6 (s) ppm; HRMS (ESI$^+$): calcd. For C$_{17}$H$_{15}$BrClN$_3$O$_2$ [M+H]$^+$ 407.0036; found 408.0136.

Example 37

5-Chloro-2-(4-(2-(4-fluorophenyl)-2-hydroxypropyl)-1H-1,2,3-triazol-1-yl)phenol (2qb)

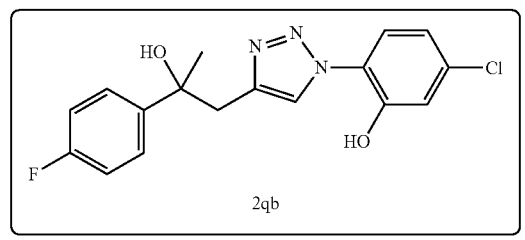 [SMILES: CC(O)(Cc1cn(-c2ccc(Cl)cc2O)nn1)c1ccc(F)cc1]

Brown color solid; 81%; (R$_f$=0.3, 30% ethyl acetate/pet. ether); $^1$H NMR (200 MHz, {MeOD+CDCl$_3$}): δ 1.55 (s, 3H), 3.20 (s, 2H), 6.87 (d, J=2.2 Hz, 1H), 6.90-6.92 (m, 1H), 6.94 (s, 1H), 6.97-7.00 (m, 2H), 7.32-7.40 (m, 2H), 7.46 (d, J=8.6 Hz, 1H), 7.69 (br. s., 1H); $^{13}$C NMR (50 MHz, {MeOD+CDCl$_3$}): δ 24.6 (q), 35.3 (t), 68.7 (s), 109.7 (d, J=21.2 Hz, 2C), 112.8 (d), 115.3 (d), 119.6(d, 2C), 121.8 (d, J=8.1 Hz, 2C), 130.2 (s), 138.2 (s), 145.1 (s, 2C), 154.4 (s), 161.9 (s) ppm; HRMS (ESI+): calcd. For C$_{17}$H$_{15}$ClFN$_3$O$_2$ [M+H]$^+$ 347.0837; found 348.0906.

Example 38

5-Chloro-2-(4-(2-(4-chlorophenyl)-2-hydroxypropyl)-1H-1,2,3-triazol-1-yl)phenol (2lb)

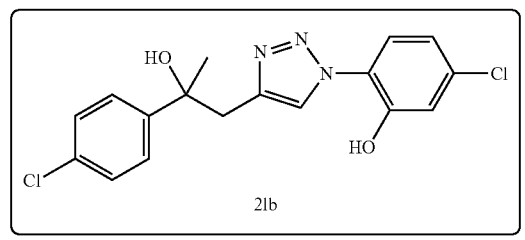 [SMILES: CC(O)(Cc1cn(-c2ccc(Cl)cc2O)nn1)c1ccc(Cl)cc1]

Orange color solid; 83%; (R$_f$=0.3, 30% ethyl acetate/pet. ether); $^1$H NMR (400 MHz, {MeOD+CDCl$_3$}): δ 51.53 (s, 3H), 3.20 (s, 2H), 6.89 (dd, J=8.7, 2.1 Hz, 1H), 7.00 (d, J=2.2 Hz, 1H), 7.22 (m, J=8.8 Hz, 2H), 7.30-7.36 (m, 2H), 7.45 (d, J=8.6 Hz, 1H), 7.72 (s, 1H); $^{13}$C NMR (101 MHz, {MeOD+CDCl$_3$}): δ 29.2 (q), 39.7 (t), 73.4 (s), 117.5 (d), 120.0 (d), 122.9 (s), 124.2 (d), 126.3 (d, 2C), 128.0 (d, 3C), 132.3 (s), 134.8 (s), 145.7 (s, 2C), 149.7 (s) ppm; HRMS (ESI+): calcd. For C$_{17}$H$_{15}$Cl$_2$N$_3$O$_2$ [M+H]$^+$ 363.0541; found 364.0610.

Example 39

2-(4-(2-(4-Bromophenyl)-2-hydroxypropyl)-1H-1,2,3-triazol-1-yl)-5-chlorophenol (2nb)

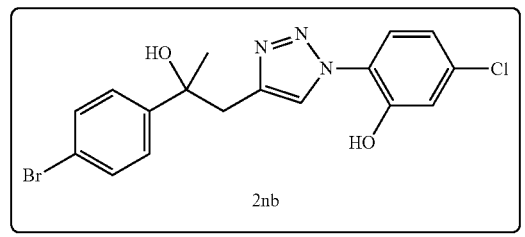 [SMILES: CC(O)(Cc1cn(-c2ccc(Cl)cc2O)nn1)c1ccc(Br)cc1]

Brown color solid; 81%; (R$_f$=0.3, 30% ethyl acetate/pet.ether); $^1$H NMR (200 MHz, {MeOD+CDCl$_3$}): δ 1.53 (s, 3H), 3.20 (s, 2H), 6.89 (dd, J=8.6, 2.2 Hz, 1H), 7.00 (d, J=2.2 Hz, 1H), 7.26-7.33 (m, 2H), 7.36 (s, 1H), 7.40 (m, 1H), 7.47 (d, J=8.6 Hz, 1H), 7.74 (s, 1H); $^{13}$C NMR (50 MHz, {MeOD+CDCl$_3$}): δ 29.3 (q), 39.6 (t), 73.5 (s), 117.7(d), 120.1 (d), 120.5 (s), 123.9(d), 126.7 (d, 2C), 131.0 (d, 2C), 134.9 (s), 146.2 (s, 2C), 149.7 (s, 2C), 154.7 (s) ppm; HRMS (ESI+): calcd. For C$_{17}$H$_{15}$BrClN$_3$O$_2$ [M+H]$^+$ 407.0036; found 408.0136.

Example 40

2-(4-(2-(4-Fluorophenyl)-2-hydroxypropyl)-1H-1,2,3-triazol-1-yl)phenol (2qd)

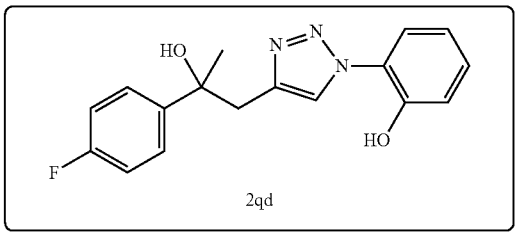 [SMILES: CC(O)(Cc1cn(-c2ccccc2O)nn1)c1ccc(F)cc1]

Brown color solid; 78%; (R$_f$=0.3, 30% ethyl acetate/pet. ether); $^1$H NMR (200 MHz, {MeOD+CDCl$_3$}): δ 1.55 (s, 3H), 3.21 (s, 2H), 6.84-7.05 (m, 4H), 7.14-7.28 (m, 1H), 7.30-7.48 (m, 3H), 7.66 (s, 1H); $^{13}$C NMR (50 MHz, {MeOD+CDCl$_3$}): δ 29.4 (q), 39.9 (t), 73.4 (s), 114.6 (d, J=21.2Hz, 2C), 117.8 (d), 119.9 (d), 122.6 (d), 123.1 (d), 123.7 (s), 126.4 (d, J=7.7 Hz, 2C), 129.7 (d), 142.8 (s), 149.0 (s, 2C), 159.1 (s), 163.9 (s) ppm; HRMS (ESI+): calcd. For C$_{17}$H$_{16}$FN$_3$O$_2$ [M+H]$^+$ 313.1227; found 314.1294.

Example 41

2-(4-(2-(4-Chlorophenyl)-2-hydroxypropyl)-1H-1,2,3-triazol-1-yl)phenol (2ld)

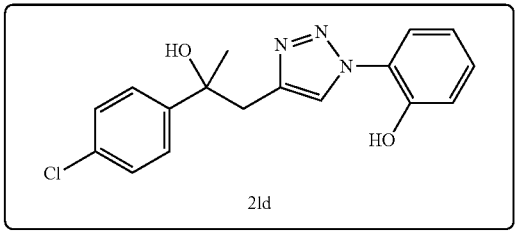 [SMILES: CC(O)(Cc1cn(-c2ccccc2O)nn1)c1ccc(Cl)cc1]

Orange color solid; 84%; (R$_f$=0.3, 30% ethyl acetate/pet. ether); $^1$H NMR (500 MHz, {MeOD+CDCl$_3$}): δ 1.56 (br. s., 3H), 3.22 (br. s., 2H), 6.89-6.97 (m, 1H), 7.00 (d, J=7.6 Hz, 1H), 7.20-7.31 (m, 3H), 7.38 (d, J=7.3 Hz, 2H), 7.54 (d, J=7.0 Hz, 1H), 7.83 (br. s., 1H); $^{13}$C NMR (125 MHz, {MeOD+CDCl$_3$}): δ 28.4 (q), 39.6 (t), 72.9 (s), 116.7(d), 119.4 (d), 123.6 (d), 123.9 (s), 124.2 (d), 126.1 (d, 2C), 127.6 (d, 2C), 129.5 (d), 131.9 (s), 142.7 (s), 145.6 (s, 2C), 148.9 (s) ppm; HRMS (ESI+): calcd. For C$_{17}$H$_{16}$ClN$_3$O$_2$ [M+H]$^+$ 329.0931; found 330.0998.

Example 42

2-(4-(2-(4-Bromophenyl)-2-hydroxypropyl)-1H-1,2,3-triazol-1-yl)phenol (2nd)

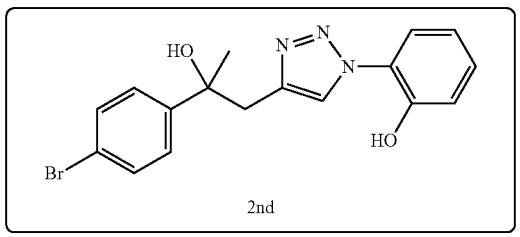 [SMILES: CC(O)(Cc1cn(-c2ccccc2O)nn1)c1ccc(Br)cc1]

Brown color solid; 84%; (R$_f$=0.3, 30% ethyl acetate/pet. ether); $^1$H NMR (200 MHz, {MeOD+CDCl$_3$}): δ 1.53 (s, 3H), 3.21 (s, 2H), 6.86-6.96 (m, 1H), 6.97-7.04 (m, 1H), 7.16-7.24 (m, 1H), 7.27-7.33 (m, 2H), 7.34-7.46 (m, 3H), 7.71 (s, 1H); $^{13}$C NMR (50 MHz, {MeOD+CDCl$_3$}): δ 29.3 (q), 39.6 (t), 73.4 (s), 117.8 (d), 120.0 (d), 120.4 (s), 122.6 (d), 123.1 (d), 126.7 (d, 2C), 129.7 (d), 131.0 (d, 2C), 146.3 (s, 2C), 149.0 (s, 2C), 160.9 (s) ppm; HRMS (ESI+): calcd. For C$_{17}$H$_{16}$BrN$_3$O$_2$ [M+H]$^+$ 373.0426; found 374.0495.

Example 43

2-(4-(2-(2,4-Difluorophenyl)-2-hydroxypropyl)-1H-1,2,3-triazol-1-yl)phenol (2kd)

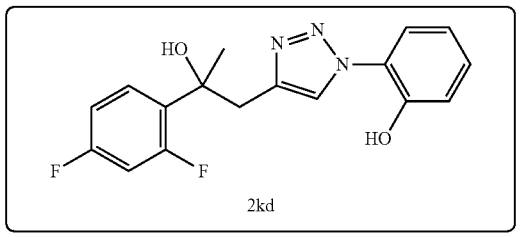 [SMILES: CC(O)(Cc1cn(-c2ccccc2O)nn1)c1ccc(F)cc1F]

Brown color solid; 82%; (R$_f$=0.3, 30% ethyl acetate/pet. ether); $^1$H NMR (200 MHz, {MeOD+CDCl$_3$}): δ 1.68 (s, 3H), 3.38 (s, 1H), 3.47 (s, 1H), 6.70-6.87 (m, 2H), 6.92-7.10 (m, 2H), 7.23-7.36 (m, 1H), 7.43-7.62 (m, 2H), 7.82 (s, 1H); $^{13}$C NMR (50 MHz, {MeOD+CDCl$_3$}): δ 28.2 (q), 37.4 (t), 72.7 (s), 103.3 (dd, J=25.6, 27.4 Hz)), 110.6 (dd, J=3.3, 23.8 Hz), 117.8 (d), 119.9 (d), 122.5 (d), 122.9 (d), 123.7 (s), 128.4 (dd, J=6.4, 9.1 Hz), 129.7 (d), 149.0 (s, 2C), 156.3 (s), 159.2 (s), 161.4 (s) ppm; HRMS (ESI+): calcd. For C$_{17}$H$_{15}$F$_2$N$_3$O$_2$ [M+H]$^+$ 331.1132; found 332.1199.

Example 44

2-(4-(2-(2,4-Dichlorophenyl)-2-hydroxypropyl)-1H-1,2,3-triazol-1-yl)phenol (2md)

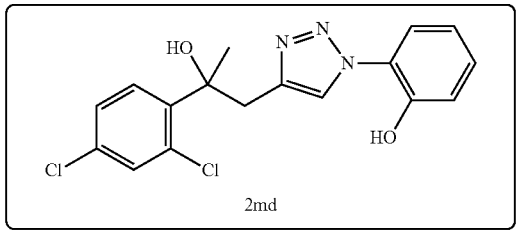 [SMILES: CC(O)(Cc1cn(-c2ccccc2O)nn1)c1ccc(Cl)cc1Cl]

Brown color solid; 81%; ($R_f$=0.3, 30% ethyl acetate/pet. ether); $^1$H NMR (200 MHz, {MeOD+CDCl$_3$}): δ 1.71 (s, 3H), 3.39 (d, J=15.0 Hz, 1H), 3.77 (d, J=14.9 Hz, 1H), 6.86-7.03 (m, 2H), 7.09-7.25 (m, 2H), 7.28-7.34 (m, 1H), 7.44 (dd, J=8.0, 1.6 Hz, 1H), 7.64 (d, J=8.6 Hz, 1H), 7.78 (s, 1H); $^{13}$C NMR (50 MHz, {MeOD+CDCl$_3$}): δ 26.8 (q), 35.9 (t), 74.1 (s), 117.5 (d), 119.8 (d), 122.8 (d), 123.1 (d), 126.8 (d), 129.3 (d), 129.6 (d), 130.4 (d), 130.9 (s), 133.0 (s), 142.1 (s), 148.9 (s, 2C), 151.6 (s) ppm; HRMS (ESI+): calcd. For $C_{17}H_{15}Cl_2N_3O_2[M+H]^+$ 363.0541; found 364.0611.

Example 45

A. Antifungal Activity

The synthesized compounds were evaluated for antifungal susceptibility by microbroth dilution method according to the recommendations of the Clinical Laboratory Standards Institute (CLSI 2008). Briefly, appropriate amount of compounds were dissolved in dimethyl sulfoxide to get 100× final strength. The stock was then diluted 1:50 in RPMI/YPG medium and 200 μl from this was added to the first row of a 96-well microtitre plate. The compounds were serially diluted two fold in successive wells to get a range of 1-128 μg/ml. Fungal yeast cells (~2×10$^3$ cfu/mL), freshly grown in YPG broth in logarithmic phase, were suspended in the medium and inoculated (100 μl) in the wells of the plate. For filamentous fungi, 2×10$^4$ spores/mL were added. The microtitre plate was incubated for 48 h, and the absorbance was measured at 600 nm by using microtitre plate reader to assess cell growth. The MIC was defined as the lowest concentration exhibiting >90% inhibition of visible growth compared to the growth of the control. Results are given in Table 1. Based on the results, compounds 2gb, 2ga, 1db, 2fa, 1ab, 2eb, 2ea, 1da, 1db were identified as promising molecules.

B. Effect of the compounds on sterol profile:

Inhibition of lanosterol 14 α-demethylase by azoles results in depletion of ergosterol. The depletion can be quantified by spectrophotometry. Briefly, Overnight grown C. albicans ATCC 24433 (1×10$^6$ cfu/ml) cells were inoculated in a series of flasks containing 50 ml of Yeast extract Peptone Glucose (YPG) broth containing 0, 0.5, 1, 2 mg of fluconazole per ml as well as 0.5 MIC and MIC of the lead compounds. The cultures were incubated for 24 h with shaking at 30° C. The stationary-phase cells were harvested by centrifugation at for 5 min and washed once with sterile distilled water. The net wet weight of the cell pellet was determined. Three milliliters of 25% alcoholic potassium hydroxide solution (25 g of OH and 35 ml of sterile distilled water, brought to 100 ml with 100% ethanol), was added to 125 mg of pellet and vortex mixed for 1 min. Cell suspensions were transferred to sterile borosilicate glass screw-cap tubes and were incubated in an 85° C. water bath for 1 h. Following incubation, tubes were allowed to cool to room temperature. Sterols were then extracted by addition of a mixture of 1 ml of sterile distilled water and 3 ml of n-heptane followed by vigorous vortex mixing for 3 min. The heptane layer was transferred to a clean borosilicate glass screw-cap tube. The sterol extract was scanned spectrophotometrically between 220 and 300 nm with a Spectrophotometer. The presence of ergosterol and the late sterol intermediate 24(28)DHF in the extracted sample resulted in a characteristic four-peaked curve. A dose-dependent decrease in the height of the absorbance peaks was evident and corresponded to decreased ergosterol concentration for fluconazole and all the tested compounds. Compounds 2fa and 2gb were most effective. The sterol profile for negative control compounds lab and 2fa was similar to control. Based on the results, compounds 2cb, 1da and 2ga were identified as potent inhibitors of lanosterol 14 α-demethylase enzyme, exerting their antifungal action through ergosterol depletion.

For compounds 2cb, 1da, 2fa, 1ab no ergosterol depletion was observed indicating different mode of action. Apart from lanosterol 14 a-demethylase inhibition, few azoles like miconazole are known to exert their antifungal action by reactive oxygen species (ROS) generation. Therefore ROS production in C. albicans ATCC 24433 was evaluated for these compounds by using dichlorofluorescin diacetate dye. Compounds 2fa, 2eb, 1da, 1ab showed dose dependent increase in ROS generation in C. albicans ATCC 24433. ROS can damage a wide range of molecules, including nucleic acids, proteins and lipids, can cause apoptosis, necrotic death and with this wide range of targets it is difficult to determine which events lead to loss of viability of cells following damage.

TABLE 1

| | Organism | | | | | |
|---|---|---|---|---|---|---|
| Compound | Candida albicans ATCC 24433 | Candida albicans ATCC 10231 | Candida glabrata NCYC 388 | Cryptococcus neoformans ATCC 34664 | Aspergillus fumigatus MCC 1046 | Aspergillus niger ATCC 10578 |
| 2gb | 16 | 16 | 8 | 8 | 8 | >128 |
| 2ga | 16 | 16 | 8 | 16 | 32 | >128 |
| 1db | 16 | 32 | 8 | 16 | >128 | >128 |
| 2eb | 64 | 32 | 32 | 32 | 32 | 128 |
| 2fa | 16 | 16 | 8 | 16 | 8 | >128 |
| 2aa | >128 | ND | 128 | 128 | >128 | >128 |
| 2db | >128 | 128 | 64 | 128 | 128 | 128 |
| 2ab | >128 | ND | 128 | >128 | 128 | >128 |
| 1ab | 32 | 32 | 32 | 32 | 32 | >128 |
| 2ia | 128 | ND | 128 | >128 | 128 | >128 |
| 1ea | 64 | ND | 128 | >128 | 128 | 64 |
| 2hb | 64 | >128 | 64 | 32 | >128 | >128 |
| 2da | 128 | ND | 128 | >128 | 128 | 64 |
| 1aa | 64 | ND | 32 | 32 | 64 | 64 |
| 2ea | 32 | 32 | 64 | 32 | 128 | 64 |
| 1ba | 128 | ND | 128 | 16 | >128 | >128 |
| 1da | 16 | 16 | 8 | 16 | >128 | >128 |
| Fluconazole | 2 | 8 | >128 | 32 | >128 | >128 |

TABLE 2

Antifungal activity of the triazole compounds against fungal human pathogens.

| Compounds | MIC values (μg/ml) | | | | | | |
|---|---|---|---|---|---|---|---|
| | C. albicans ATCC 24433 | C. albicans ATCC 10231 | C. neoformans ATCC 34664 | C. glabrata NCYC 388 | C. tropicalis ATCC 750 | A. niger ATCC 10578 | A. fumigatus MCC 1046 |
| 3ac | 8 | ND | 128 | ND | 128 | 128 | 64 |
| 3bc | 16 | 8 | 16 | 16 | 32 | 64 | 64 |
| 3cc | 128 | ND | >256 | ND | >256 | >256 | >256 |
| 3dc | 64 | ND | 256 | ND | >256 | 256 | 128 |
| 3ec | 8 | ND | 128 | ND | 128 | 128 | 64 |
| 3fc | 8 | 16 | 64 | 64 | 128 | 128 | 64 |
| 3da | 32 | 32 | 64 | 64 | 128 | 128 | 64 |
| 3ea | 16 | 8 | 32 | 16 | 64 | 64 | 64 |
| 3fa | 4 | ND | 32 | ND | 64 | 32 | 16 |
| 3db | 16 | ND | 128 | ND | 128 | 64 | 32 |
| 3eb | 32 | 16 | 32 | 32 | 64 | 64 | 64 |
| 3fb | 16 | 16 | 32 | 32 | 64 | 64 | 64 |
| 3dd | 64 | ND | 256 | ND | >256 | 256 | 256 |
| 3ed | 8 | ND | 128 | ND | 256 | 128 | 64 |
| 3fd | 32 | ND | 128 | ND | 256 | 128 | 128 |
| 3ad | 8 | ND | 128 | ND | 256 | 128 | 128 |
| 3bd | 8 | ND | 32 | ND | 64 | 32 | 16 |
| 3aa | 32 | 32 | 64 | 32 | 128 | 128 | >256 |
| 3ba | 32 | ND | >256 | ND | >256 | >256 | >256 |
| 3ga | 64 | 16 | 64 | 16 | >256 | >256 | >256 |
| 3ab | 16 | 32 | 32 | 32 | 64 | 64 | 64 |
| 3bb | 4 | 16 | 8 | 16 | 32 | 32 | 16 |
| 3cb | 16 | ND | >256 | ND | >256 | >256 | >256 |

ND—Not done

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

Advantages of Invention a. Synthesis of newer azole derivatives.
b. The lead molecules identified showed better in vitro antifungal activity against most of the pathogenic fungi as compared to fluconazole.
c. The compounds inhibited ergosterol biosynthesis, a sterol absent in humans; hence they will not be toxic or have side-effects.

The invention claimed is:
1. An antifungal compound of the formula (I)

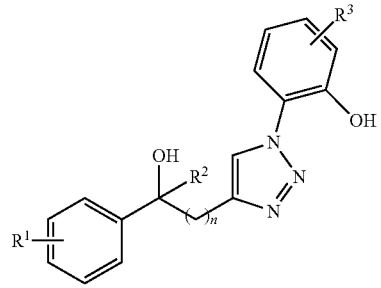

Formula (I)

Wherein, $R_1$ is fluorine, chlorine, bromine, $CF_3$, hydrogen, dimethylamino or alkyl;
$R_2$ is alkyl, phenyl, $CF_3$ or hydrogen;
$R_3$ is hydrogen or halogen, wherein the halogen is selected from fluorine, chlorine or bromine;
and n is 0 or 1.

2. A compound which is
i. 4-Chloro-2-(4-((3,5-dimethylphenyl)(hydroxy)methyl)-1H-1,2,3-triazol-1-yl)phenol (1aa),
ii. 2-(4-((3,5-Bis(trifluoromethyl)phenyl)(hydroxy)methyl)-1H-1,2,3-triazol-1-yl)-4-chlorophenol(1ba),
iii. 4-Chloro-2-(4-(1-hydroxy-1-phenylpropyl)-1H-1,2,3-triazol-1-yl)phenol,
iv. 5-Chloro-2-(4-((3,5-dimethylphenyl)(hydroxy)methyl)-1H-1,2,3-triazol-1-yl)phenol(1ab),
v. 5-Chloro-2-(4-(1-hydroxy-1-phenylethyl)-1H-1,2,3-triazol-1-yl)phenol(2cb),
vi. 4-Chloro-2-(4-(2-hydroxy-2-phenylethyl)-1H-1,2,3-triazol-1-yl)phenol(1ea),
vii. 5-Chloro-2-(4-(2-hydroxy-2-phenylethyl)-1H-1,2,3-triazol-1-yl)phenol(1eb),
viii. 4-Chloro-2-(4-(2-hydroxy-2-phenylpropyl)-1H-1,2,3-triazol-1-yl)phenol(2fa),
ix. 5-Chloro-2-(4-(2-hydroxy-2-phenylpropyl)-1H-1,2,3-triazol-1-yl)phenol(2fb),
x. 4-Chloro-2-(4-(2-hydroxy-2-phenylbutyl)-1H-1,2,3-triazol-1-yl)phenol(2ga),
xi. 5-Chloro-2-(4-(2-hydroxy-2-phenylbutyl)-1H-1,2,3-triazol-1-yl)phenol(2gb),
xii. 4-chloro-2-(4-(2-hydroxy-2-phenylhexyl)-1H-1,2,3-triazol-1-yl)phenol(2ha),
xiii. 4-Chloro-2-(4-(2-hydroxy-2,2-diphenylethyl)-1H-1,2,3-triazol-1-yl)phenol(2ia),
xiv. 5-Chloro-2-(4-(2-hydroxy-2,2-diphenylethyl)-1H-1,2,3-triazol-1-yl)phenol(2ib), xv. 2-(4-(2-(3,5-Bis(trifluoromethyl)phenyl)-2-hydroxyethyl)-1H-1,2,3-triazol-1-yl)-4-chlorophenol(1ja),
xvi. 2-(4-(2-(3,5-Bis(trifluoromethyl)phenyl)-2-hydroxyethyl)-1H-1,2,3-triazol-1-yl)-5-chlorophenol(1jb),
xvii. 2-(4-(2-(3,5-Bis(trifluoromethyl)phenyl)-2-hydroxypropyl)-1H-1,2,3-triazol-1-yl)-4-chlorophenol (2sa),
xviii. 2-(4-(2-(3,5-Bis(trifluoromethyl)phenyl)-2-hydroxypropyl)-1H-1,2,3-triazol-1-yl)-5-chlorophenol (2sb),
xix. 4-Chloro-2-(4-(2-(2,4-difluorophenyl)-2-hydroxypropyl)-1H-1,2,3-triazol-1-yl)phenol(2ka),
xx. 4-Chloro-2-(4-(2-(2,4-dichlorophenyl)-2-hydroxypropyl)-1H-1,2,3-triazol-1-yl)phenol (2ma),
xxi. 4-Chloro-2-(4-(2-(4-(dimethylamino)phenyl)-2-hydroxycthyl)-1H-1,2,3-triazol-1-yl)phenol (2pa),
xxii. 5-Chloro-2-(4-(2-(2,4-difluorophenyl)-2-hydroxypropyl)-1H-1,2,3-triazol-1-yl)phenol (2kb),
xxiii. 5-Chloro-2-(4-(2-(2,4-dichlorophenyl)-2-hydroxypropyl)-1H-1,2,3-triazol-1-yl)phenol (2mb),
xxiv. 5-Chloro-2-(4-(2-(2-fluoro-4-(trifluoromethyl)phenyl)-2-hydroxyethyl)-1H-1,2,3-triazol-1-yl)phenol (2ob),
xxv. 2-(4-(2-(2,4-Difluorophenyl)-2-hydroxypropyl)-1H-1,2,3-triazol-1-yl)-5-fluorophenol (2kc),
xxvi. 2-(4-(2-(2,4-Dichlorophenyl)-2-hydroxypropyl)-1H-1,2,3-triazol-1-yl)-5-fluorophenol (2mc),
xxvii. 5-Fluoro-2-(4-(2-(2-fluoro-4-(trifluoromethyl)phenyl)-2-hydroxyethyl)-1H-1,2,3-triazol-1-yl)phenol (2oc),
xxviii. 5-Fluoro-2-(4-(2-(4-fluorophenyl)-2-hydroxypropyl)-1H-1,2,3-triazol-1-yl)phenol (2qc),
xxix. 2-(4-(2-(4-Chlorophenyl)-2-hydroxypropyl)-1H-1,2,3-triazol-1-yl)-5-fluorophenol (2lc),
xxx. 2-(4-(2-(4-Bromophenyl)-2-hydroxypropyl)-1H-1,2,3-triazol-1-yl)-5-fluorophenol (2nc),
xxxi. 4-Chloro-2-(4-(2-(4-fluorophenyl)-2-hydroxypropyl)-1H-1,2,3-triazol-1-yl)phenol (2qa),
xxxii. 4-Chloro-2-(4-(2-(4-chlorophenyl)-2-hydroxypropyl)-1H-1,2,3-triazol-1-yl)phenol (2la),
xxxiii. 2-(4-(2-(4-Bromophenyl)-2-hydroxypropyl)-1H-1,2,3-triazol-1-yl)-4-chlorophenol (2na),
xxxiv. 5-Chloro-2-(4-(2-(4-fluorophenyl)-2-hydroxypropyl)-1H-1,2,3-triazol-1-yl)phenol (2qb),
xxxv. 5-Chloro-2-(4-(2-(4-chlorophenyl)-2-hydroxypropyl)-1H-1,2,3-triazol-1-yl)phenol (2lb),
xxxvi. 2-(4-(2-(4-Bromophenyl)-2-hydroxypropyl)-1H-1,2,3-triazol-1-yl)-5-chlorophenol (2nb),
xxxvii. 2-(4-(2-(4-Fluorophenyl)-2-hydroxypropyl)-1H-1,2,3-triazol-1-yl)phenol (2qd),
xxxviii. 2-(4-(2-(4-Chlorophenyl)-2-hydroxypropyl)-1H-1,2,3-triazol-1-yl)phenol (2ld),
xxxix. 2-(4-(2-(4-Bromophenyl)-2-hydroxypropyl)-1H-1,2,3-triazol-1-yl)phenol (2nd),
xl. 2-(4-(2-(2,4-Difluorophenyl)-2-hydroxypropyl)-1H-1,2,3-triazol-1-yl)phenol (2kd) or
xli. 2-(4-(2-(2,4-Dichlorophenyl)-2-hydroxypropyl)-1H-1,2,3-triazol-1-yl)phenol (2md).

3. A pharmaceutical composition comprising an antifungal compound of formula (I) according to claim 1, in combination with at least one pharmaceutical excipient.

4. A method for treating a fungal infection in a subject, wherein the method comprises administering to the said subject an effective amount of an antifungal compound of formula (I) according to claim 1.

5. The method of claim 4, wherein said compound of formula (I) is administered in combination with at least one pharmaceutical excipient.

6. A process for the preparation of a triazole antifungal compound of claim 2, wherein the process comprises the steps of:
a) Adding sodium ascorbate (0.95 eq) and copper (II) sulfate (0.2 eq) to a solution of 2-azidophenol 5

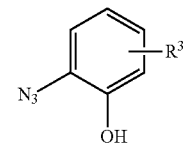

5 wherein $R^3$ is hydrogen or halogen, wherein the halogen is selected from fluorine, chlorine or bromine,
and an alkyne 4a, 4b, 4c, 4d, 7e, 7f, 7g, 7h, 7i, 7j, 7k, 7l, 7m, 7n, 7o, 7p, 7q, 7r or 7s

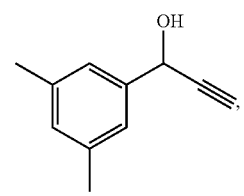

4a

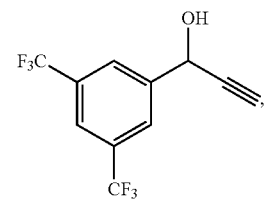

4b

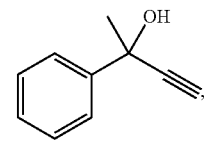

4c

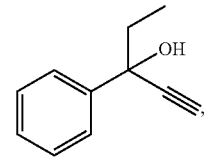

4d

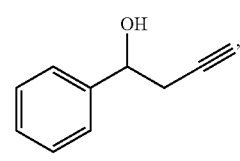

7e

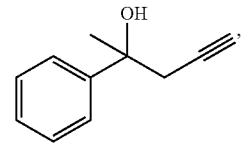

7f

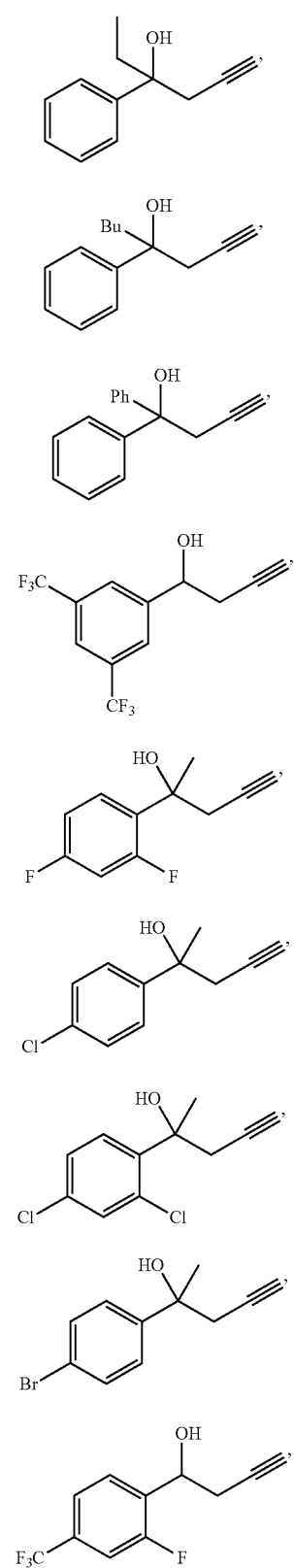

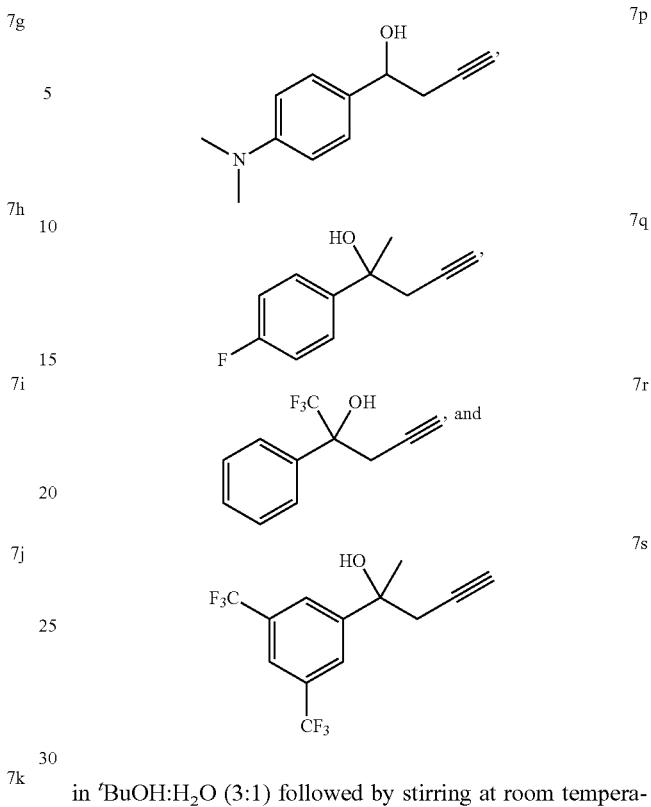

in ᵗBuOH:H₂O (3:1) followed by stirring at room temperature (25°-30° C.) for a period of time ranging between 10 min-1 hour to obtain brick reddish reaction mixture; and b) Diluting and extracting the reaction mixture obtained in step (a) followed by purifying and drying to get the pure product.

7. The process according to claim 6, wherein said 2-azidophenol 5 is selected from the group consisting of

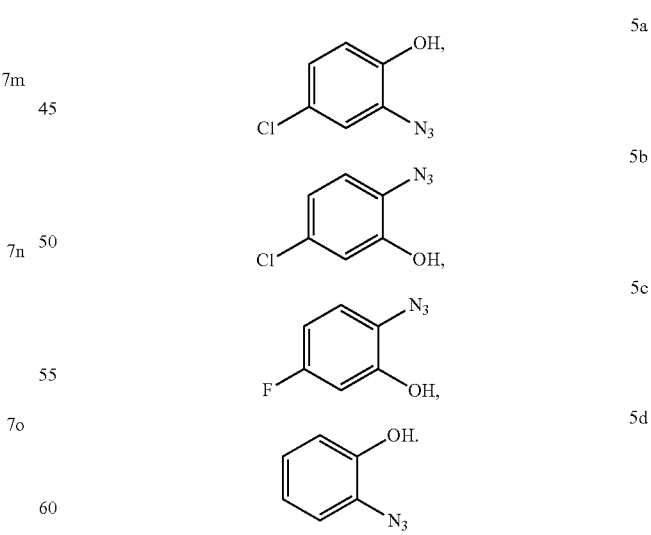

* * * * *